(12) United States Patent
Geva et al.

(10) Patent No.: US 12,127,843 B2
(45) Date of Patent: Oct. 29, 2024

(54) DETACHABLE ELECTROCARDIOGRAPHY DEVICE

(71) Applicant: LIFEWATCH TECHNOLOGIES LTD., Rehovot (IL)

(72) Inventors: Yacov Geva, London (GB); Nir Geva, Nes Ziona (IL); Yossi Lovton, Nes Ziona (IL); Benny Tal, Ashkelon (IL)

(73) Assignee: Lifewatch Technologies Ltd.

( * ) Notice: Subject to any disclaimer, the term of this patent is extended or adjusted under 35 U.S.C. 154(b) by 989 days.

(21) Appl. No.: 16/862,138

(22) Filed: Apr. 29, 2020

(65) Prior Publication Data

US 2020/0305754 A1 Oct. 1, 2020

Related U.S. Application Data

(63) Continuation of application No. 14/911,243, filed as application No. PCT/IL2014/050853 on Sep. 29, 2014, now Pat. No. 10,674,926, which is a continuation of application No. 14/040,750, filed on Sep. 30, 2013, now abandoned.

(51) Int. Cl.
*A61B 5/282* (2021.01)
*A61B 5/00* (2006.01)
*A61B 5/259* (2021.01)
*A61B 5/274* (2021.01)
(Continued)

(52) U.S. Cl.
CPC ............ *A61B 5/282* (2021.01); *A61B 5/0006* (2013.01); *A61B 5/259* (2021.01); *A61B 5/274* (2021.01); *A61B 5/303* (2021.01); *A61B 5/316* (2021.01); *A61B 5/6823* (2013.01); *A61B 2560/0443* (2013.01); *A61B 2560/0468* (2013.01); *A61B 2562/164* (2013.01); *A61B 2562/182* (2013.01);
(Continued)

(58) Field of Classification Search
CPC ......... A61B 5/282; A61B 5/259; A61B 5/274; A61B 5/303; A61B 5/316; A61B 5/0006; A61B 5/6823; A61B 2560/0443; A61B 2560/0468; A61B 2562/164; A61B 2562/182; A61B 2562/222; A61B 2562/227
See application file for complete search history.

(56) References Cited

U.S. PATENT DOCUMENTS 5,042,481 A 8/1991 Suzuki
6,117,077 A 9/2000 Del Mar
(Continued)

*Primary Examiner* — Adam Z Minchella

(57) ABSTRACT

An electrocardiographic system includes first and second parts. The first part includes: a first housing having a first bottom layer that is elastic with an underside having an adhesive material; and a first set of electrodes located within the first housing, where the first set of electrodes includes at least one first electrode. The second part includes: a second housing having a second bottom layer with an underside having an adhesive material; a second set of electrodes located within the second housing, where the second set of electrodes includes at least one second electrode; a mechanical adaptor configured to be detachably connected to a electrocardiographic device that includes a processor and a wireless transmitter; and an electrical connector arranged to be detachably connected to the electrocardiographic device and to electrically couple the electrocardiographic device to conductors that convey signals from the first and second sets of electrodes.

12 Claims, 23 Drawing Sheets

(51) Int. Cl.
　　　*A61B 5/30*　　　(2021.01)
　　　*A61B 5/316*　　(2021.01)
(52) U.S. Cl.
　　　CPC ... *A61B 2562/222* (2013.01); *A61B 2562/227* (2013.01)

(56) References Cited

U.S. PATENT DOCUMENTS

| | | | |
|---|---|---|---|
| 6,546,285 | B1 | 4/2003 | Owen |
| 6,605,046 | B1 | 8/2003 | Del Mar |
| 8,954,129 | B1* | 2/2015 | Schlegel ............... A61B 5/256 |
| | | | 600/382 |
| 2004/0176674 | A1 | 9/2004 | Nazeri |
| 2005/0143669 | A1 | 6/2005 | Matsumura |
| 2005/0261598 | A1* | 11/2005 | Banet .................. A61B 5/0205 |
| | | | 600/513 |
| 2007/0027388 | A1* | 2/2007 | Chou ................... A61B 5/0002 |
| | | | 600/382 |
| 2007/0203558 | A1 | 8/2007 | Jonsen |
| 2008/0288026 | A1 | 11/2008 | Cross et al. |
| 2010/0042012 | A1 | 2/2010 | Alhussiny |
| 2011/0160601 | A1 | 6/2011 | Wang |
| 2011/0237922 | A1* | 9/2011 | Parker, III ........... A61B 5/1112 |
| | | | 600/382 |
| 2012/0197144 | A1 | 8/2012 | Christ |
| 2013/0019383 | A1 | 1/2013 | Korkala |
| 2013/0331721 | A1* | 12/2013 | Battaglia ................ A61B 5/316 |
| | | | 600/523 |
| 2014/0094674 | A1 | 4/2014 | Nurmikko |
| 2015/0150471 | A1 | 6/2015 | Balda |
| 2017/0035314 | A1 | 2/2017 | Kronstedt |

* cited by examiner

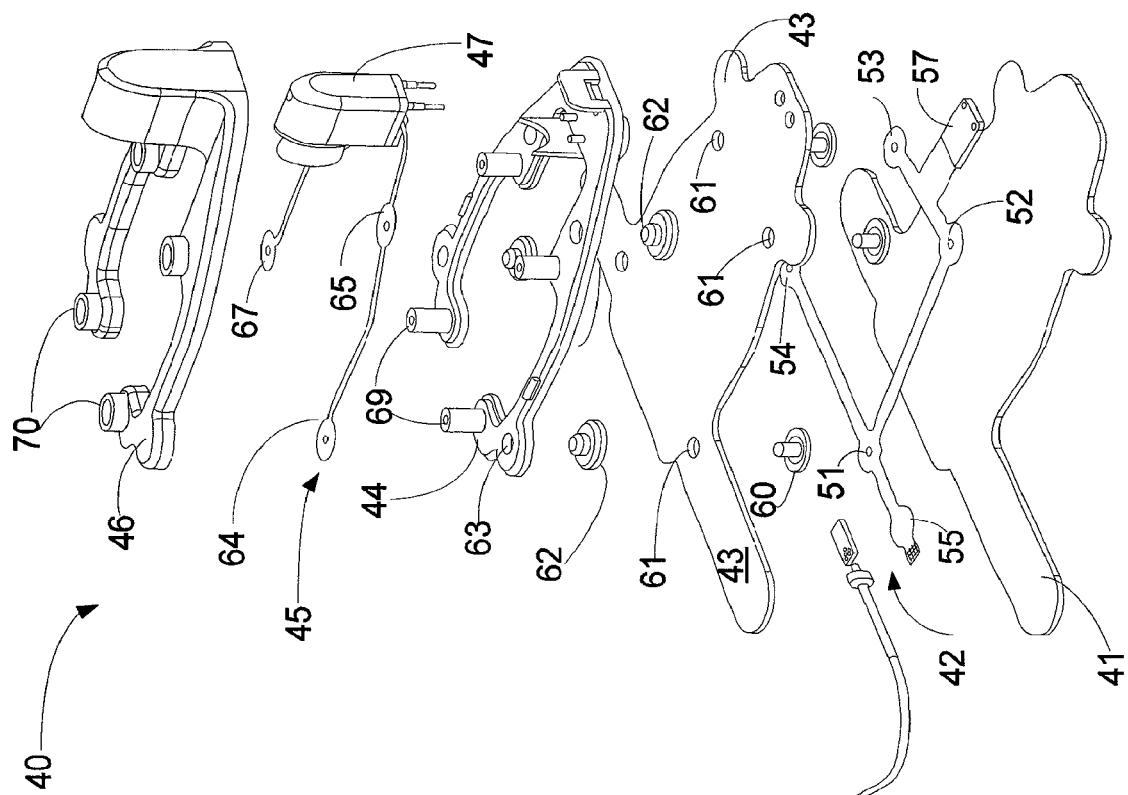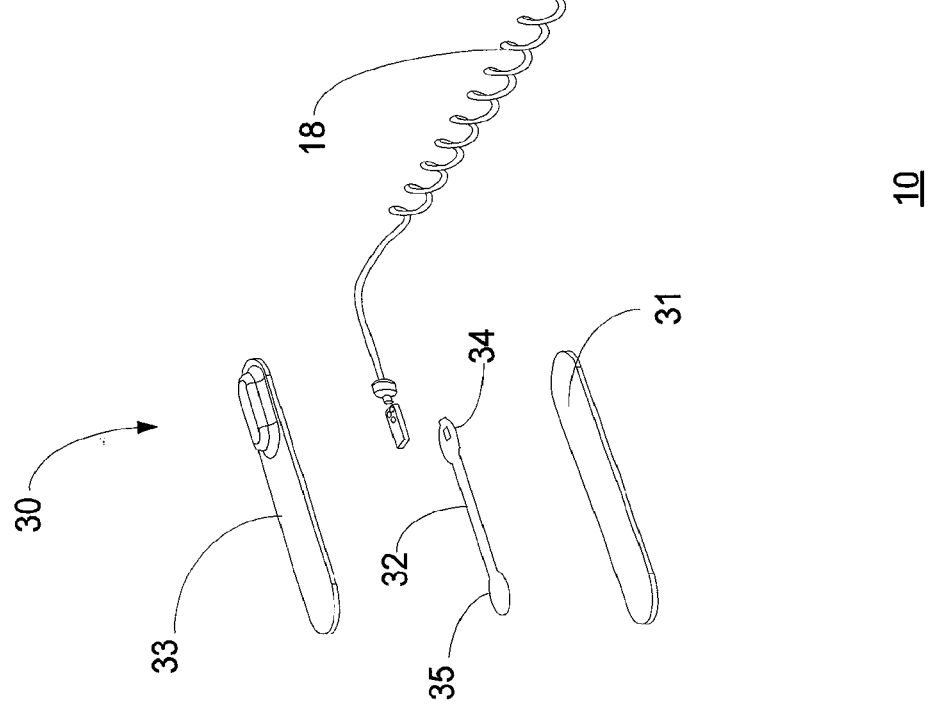
FIG. 5

510 detecting electrocardiographic signals, wherein each of the electrocardiographic signals is detected between a different pair of electrodes out of a group of electrodes that substantially consists of electrodes located on a body of a patient substantially at the following electrodes connection locations: (a) in the second intercostal space to the right of the sternum, (b) on the intersection of the left medial clavicular line and the fifth intercostal space, (c) on the intersection of the fifth intercostal space and left median-axillar line.

511 detecting at least one of the electrocardiographic signals by implementing a reference electrode that is substantially located in proximity to an electrode of the group of electrodes that is located on the second intercostal space to the right of the sternum.

520 amplifying at least one of the electrocardiographic signals.

530 receiving ECG signals, wherein each of the electrocardiographic signals is detected between a different pair of electrodes out of a group of electrodes that substantially consists of electrodes located on a body of a patient substantially at the following electrodes connection locations: (a) in the second intercostal space to the right of the sternum, (b) on the intersection of the left medial clavicular line and the fifth intercostal space, (c) on the intersection of the fifth intercostal space and left median-axillar line.

540 providing electrocardiographic information in response to the electrocardiographic signals.

550 processing the electrocardiographic information so as to provide electrocardiographically assessable information.

560 transmitting the electrocardiographic information.

561 transmitting the electrocardiographic information wirelessly.

500     FIG. 13

530 receiving electrocardiographic signals, wherein each of the electrocardiographic signals is detected between a different pair of electrodes out of a group of electrodes that substantially consists of electrodes located on a body of a patient substantially at the following electrodes connection locations: (a) in the second intercostal space to the right of the sternum, (b) on the intersection of the left medial clavicular line and the fifth intercostal space, (c) on the intersection of the fifth intercostal space and left median-axillar line.

531 receiving the electrocardiographic signals detected between different pairs of electrodes out of the group of electrodes, wherein a first electrode of the group of electrodes is substantially located on the intersection of the fifth intercostal space and left median-axillar line, and a second electrode of the group of electrodes is located in an immediate proximity to the first electrode, wherein each of the three electrocardiographic signals is detected between a pair of electrodes selected from the group of electrodes which is different from a pair consisting of the first electrode and the second electrode.

532 receiving the electrocardiographic signals detected between different pairs of electrodes out of the group of electrodes, wherein the group of electrodes substantially consist of: (a) the first electrode; (b) the second electrode; (c) a third electrode that is substantially located on the body of the patient in the second intercostal space to the right of the sternum; and (d) a fourth electrode that is substantially located on the body of the patient on the second intercostal space to the right of the sternum; wherein: (a) a first ECG signal is detected between the third electrode and the first electrode; (b) a second ECG signal is detected between the third electrode and the fourth electrode; and (c) a third ECG signal is detected between the fourth electrode and the second electrode.

533 receiving the electrocardiographic signals by a compact mobile electrocardiographic system.

534 receiving the electrocardiographic signals detected between different pairs of electrodes out of the group of electrodes, wherein each of the electrodes of the group of electrodes is adapted to be detachably attached by the patient to the body of the patient at one of the electrode connection locations.

FIG. 14

910 detecting at least one electrocardiographic signal of three electrocardiographic signals each of which is detected between a different pair of electrodes out of a electrode group that consists of three electrodes located on a body of a patient 911 detecting the at least one electrocardiographic signal by implementing a reference electrode . The reference electrode may be near to any one of the three electrodes.

920 amplifying at least one of the electrocardiographic signals 930 receiving three electrocardiographic signals, wherein each of the three electrocardiographic signals is detected between a different pair of electrodes out of a electrode group that consists of three electrodes located on a body of a patient 931 receiving the three electrocardiographic signals, wherein each of the three electrocardiographic signals is detected between a different pair of electrodes out of a electrode group that substantially consists of three electrodes located on a body of a patient substantially at the following electrodes connection locations: (a) in the second intercostal space to the right of the sternum, (b) on the intersection of the left medial clavicular line and the fifth intercostal space, (c) on the intersection of the fifth intercostal space and left median-axillar line.

940 processing the three electrocardiographic signals, to determine a cardiological problem status in response to the three electrocardiographic signals 941 processing the three electrocardiographic signals to provide electrocardiographic information 942 processing the electrocardiographic information, so as to provide the cardiological problem indication 950 providing a cardiological problem indication in response to the three electrocardiographic signals 951 providing the electrocardiographic information in response to the three electrocardiographic signals 952 providing an acute arrhythmias cardiological problem indication in response to the three electrocardiographic signals 953 providing an ischemia cardiological problem indication in response to the three electrocardiographic signals 960 transmitting the cardiological problem indication 961 transmitting the cardiological problem indication wirelessly

900     FIG. 16

Receiving by a electrocardiographic device of an electrocardiographic system, signals obtained from a first part and a second part of the electrocardiographic system; wherein the first part comprises: a first housing that comprises of a first bottom layer that is elastic and has an underside provided with an adhesive material; a first set of electrodes that is located within the first housing; wherein the first set of electrodes comprises at least one first electrode; wherein the second part comprises a second housing that comprises a second bottom layer that has an underside provided with an adhesive material; a second set of electrodes that are located within the second housing; wherein the second set of electrodes comprises at least one second electrode; a mechanical adaptor that is arranged to be detachably connected to the electrocardiographic device that comprises a processor and a wireless transmitter; and an electrical connector that is detachably is arranged to be detachably connected to the electrocardiographic device and to electrically couple the electrocardiographic device to conductors that convey signals from the first and second sets of electrodes. 1010

Providing, by the electrocardiograph device, electrocardiographic information in response to the electrocardiographic signals. 1020

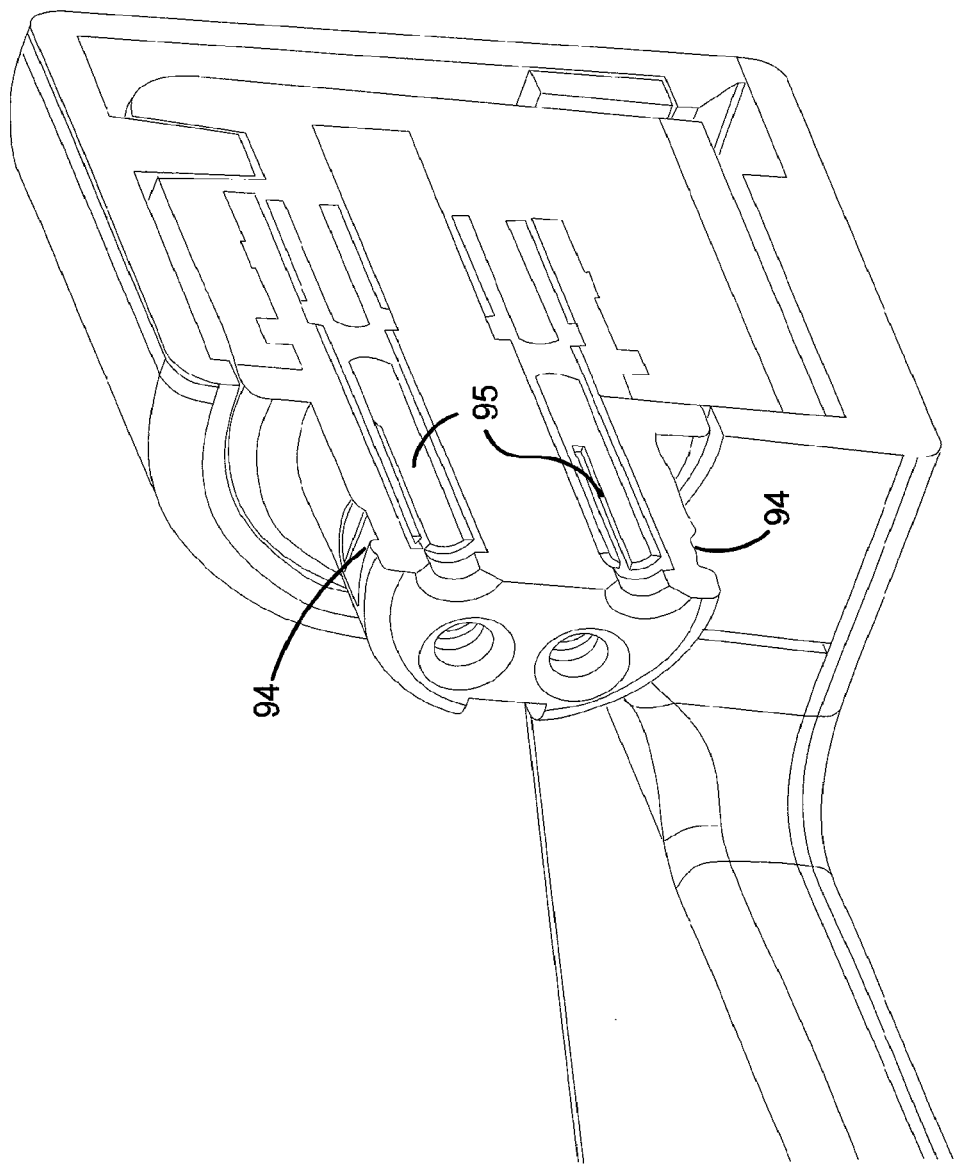

DETACHABLE ELECTROCARDIOGRAPHY DEVICE

CROSS-REFERENCE TO RELATED APPLICATION

This application is a continuation of U.S. patent application Ser. No. 14/911,243, filed Feb. 9, 2016, which is a national stage application filed under 35 U.S.C. § 371 of International Patent Application No. PCT/IL2014/050853, filed on Sep. 29, 2014, which is a continuation of U.S. patent application Ser. No. 14/040,750, filed Sep. 30, 2013, each of which is incorporated by reference herein in its entirety.

FIELD OF THE INVENTION

The invention relates to a detachable electrocardiography device and a method for electrocardiography.

BACKGROUND OF THE INVENTION

During the last couple of years the importance of health monitoring has increased. Remote health monitoring allows the patients to continue with their daily routine without being restricted to hospitals of dedicated laboratories.

There is a growing need to provide efficient health monitors that are compact and are accurate.

SUMMARY OF THE INVENTION

According to various embodiments of the invention there is provided a detachable electrocardiogram that may include a first part that may include a first housing that may include a first bottom layer that is elastic and has an underside provided with an adhesive material; a first set of electrodes that is located within the first housing; wherein the first set of electrodes may include at least one first electrode; a second part that may include a second housing that may include a second bottom layer that has an underside provided with an adhesive material; a second set of electrodes that are located within the second housing; wherein the second set of electrodes may include at least one second electrode; a mechanical adaptor that may be arranged to be detachably connected to a electrocardiographic device that may include a processor and a wireless transmitter; and an electrical connector that may be arranged to be detachably connected to the electrocardiographic device and to electrically couple the electrocardiographic device to conductors that convey signals from the first and second sets of electrodes.

The detachable electrocardiographic system may include the electrocardiograph device.

The electrocardiograph device may include a processor for processing electrical signals from the first and second sets of electrodes and a wireless transmitter for transmitting an outcome of the processing of the electrical signals.

The conductors may include a shielded wire that electrically couples the first set of electrodes to the second part of the detachable electrocardiograph system.

The second part may include an intermediate flexible layer; wherein the electrodes may be positioned between the second bottom portion and the intermediate flexible layer.

The detachable electrocardiographic system may include a first electrical circuit that may include the second set of electrodes and a first set of conductors that are electrically coupled to electrodes of the first and second sets of electrodes.

The first electrical circuit may include a ground conductor that is electrically coupled to a ground input of the electrical connector.

The detachable electrocardiographic system may include a second electrical circuit that may include a second set of conductors that are electrically coupled to the first set of conductors and to the electrical connector.

The intermediate flexible layer and a base layer of the mechanical adaptor may be positioned between the first and second electrical circuit, and wherein the inter-layer conductors extend through the intermediate flexible layer and the base layer of the mechanical adaptor.

The conductors of the first and second sets of conductors may be are coupled to each other via inter-layer conductors that are passed through the intermediate flexible layer and the base layer of the mechanical adaptor.

The inter-layer conductors may include metallic bolts.

The metallic bolts may include a first set of bolts and a second set of bolts; wherein the second set of bolts are coupled between the second set of conductors and the first set of bolts and wherein the first set of bolts are coupled between the second set of conductors and the first set of conductors.

Each bolt of the first set of bolts may be electrically coupled to a bolt of the second set of bolts to provide a pair of coupled bolts; wherein each pair of coupled bolts is coupled to a single electrode out of the electrodes of the first and second set of electrodes.

Each bolt of the first set of bolts may penetrate through an opening formed in the intermediate layer and each bolt of the second set of bolts penetrates through the openings formed in the base layer of the mechanical adaptor.

The second electrical circuit may be positioned between the base layer of the mechanical adaptor and an upper layer of the mechanical adaptor.

The first and second sets of electrodes may essentially consist of electrodes located on a body of a patient substantially at the following electrodes connection locations (a) in the second intercostal space to the right of the sternum, (b) on the intersection of the left medial clavicular line and the fifth intercostal space, (c) on the intersection of the fifth intercostal space and left median-axillar line.

The first and second sets of electrodes may essentially consist of (a) a first electrode that is substantially located on the intersection of the fifth intercostal space and left median-axillar line; (b) a second electrode that is substantially located on the body of the patient in the second intercostal space to the right of the sternum; and (c) a third electrode that is substantially located on the body of the patient on the intersection of the left medial clavicular line and the fifth intercostal space; wherein (a) a first electrocardiographic signal is detected between the second electrode and the first electrode; (b) a second electrocardiographic signal is detected between the second electrode and the third electrode; and (c) a third electrocardiographic signal is detected between the third electrode and the first electrode.

The first and second sets of electrodes may essentially consist of electrodes located on a body of a patient substantially at the following electrode connection locations (a) in the second intercostal space to the right of the sternum, (b) on the intersection of the left medial clavicular line and the fifth intercostal space, (c) on the intersection of the fifth intercostal space and left median-axillar line, and (d) a reference electrode that is substantially located in proximity to an electrode of the electrode group that is located in the second intercostal space to the right of the sternum.

The second set electrodes may essentially consist of electrodes located on a body of a patient substantially at the following electrode connection locations (a) on the intersection of the left medial clavicular line and the fifth intercostal space and (b) on the intersection of the fifth intercostal space and left median-axillar line, and wherein the first set of electrodes essentially consists of an electrode and a reference electrode located on the body of the patient substantially at a second intercostal space to the right of the sternum.

The first set electrodes may essentially consist of electrodes located on a body of a patient substantially at the following electrode connection locations (a) on the intersection of the left medial clavicular line and the fifth intercostal space and (b) on the intersection of the fifth intercostal space and left median-axillar line, and wherein the second set of electrodes essentially consists of an electrode and a reference electrode located on the body of the patient substantially at substantially a second intercostal space to the right of the sternum.

The detachable electrocardiographic system may include shielding elements for shielding the conductors that convey signals from the first and second sets of electrodes to the electrical connector.

The electrical connector may include a housing that is connected to the base layer of the mechanical adaptor and may include a socket that may be arranged to move in relation to base layer of the mechanical adaptor There may be provided a method for electrocardiographic detecting, the method may include receiving electrocardiographic signals by a electrocardiographic device of an electrocardiogram; the electrocardiogram further may include an adaptor that may include a first part and a second part; wherein the first part may include a first housing that may include first bottom layer that is elastic and has an underside provided with an adhesive material; a first set of electrodes that is located within the first housing; wherein the first set of electrodes may include at least one first electrode; wherein the second part may include a second housing that may include a second bottom layer that has an underside provided with an adhesive material; a second set of electrodes that are located within the second housing; wherein the second set of electrodes may include at least one second electrode; a mechanical adaptor that may be arranged to be detachably connected to the electrocardiographic device that may include a processor and a wireless transmitter; and an electrical connector that may be arranged to be detachably connected to the electrocardiographic device and to electrically couple the electrocardiographic device to conductors that convey signals from the first and second sets of electrodes; and providing, by the electrocardiographic device, electrocardiographic information in response to the electrocardiographic signals.

Each of the electrocardiographic signals is detected between a different pair of electrodes out of an electrode group that substantially consists of electrodes located on a body of a patient substantially at the following electrodes connection locations (a) in the second intercostal space to the right of the sternum, (b) on the intersection of the left medial clavicular line and the fifth intercostal space, (c) on the intersection of the fifth intercostal space and left median-axillar line.

The receiving may include receiving the electrocardiographic signals detected between different pairs of electrodes out of the electrode group, wherein the electrode group substantially consist of (a) a first electrode that is substantially located on the intersection of the fifth intercostal space and left median-axillar line; (b) a third electrode that is substantially located on the body of the patient in the second intercostal space to the right of the sternum; and (c) a fourth electrode that is substantially located on the body of the patient on the intersection of the left medial clavicular line and the fifth intercostal space; wherein (a) a first electrocardiographic signal is detected between the third electrode and the first electrode; (b) a second electrocardiographic signal is detected between the third electrode and the fourth electrode; and (c) a third electrocardiographic signal is detected between the fourth electrode and the second electrode.

The receiving may follow a stage of detecting the electrocardiographic signals, wherein the detecting further may include detecting at least one of the electrocardiographic signals by implementing a reference electrode that is substantially located in proximity to an electrode of the electrode group that is located on the intersection of the fifth intercostal space and left median-axillar line.

BRIEF DESCRIPTION OF THE DRAWINGS

The foregoing and other objects, features, and advantages of the present invention will become more apparent from the following detailed description when taken in conjunction with the accompanying drawings. In the drawings, similar reference characters denote similar elements throughout the different views, in which:

FIG. 5 is an exploded view of an electrocardiograph system without an electrocardiograph device position at a lower configuration according to an embodiment of the invention;

FIGS. 13 and 14 illustrate a method for electrocardiographic detecting, according to an embodiment of the invention;

FIG. 16 illustrates a method for providing a cardiological problem indication, according to an embodiment of the invention;

FIG. 17 illustrates a method for providing a cardiological problem indication, according to an embodiment of the invention;

FIG. 25 is a cross sectional view of a portion of the mechanical adaptor that comprises a female connector according to an embodiment of the invention.

DETAILED DESCRIPTION OF THE DRAWINGS

Electro-Mechanical Arrangement

Figure 1:
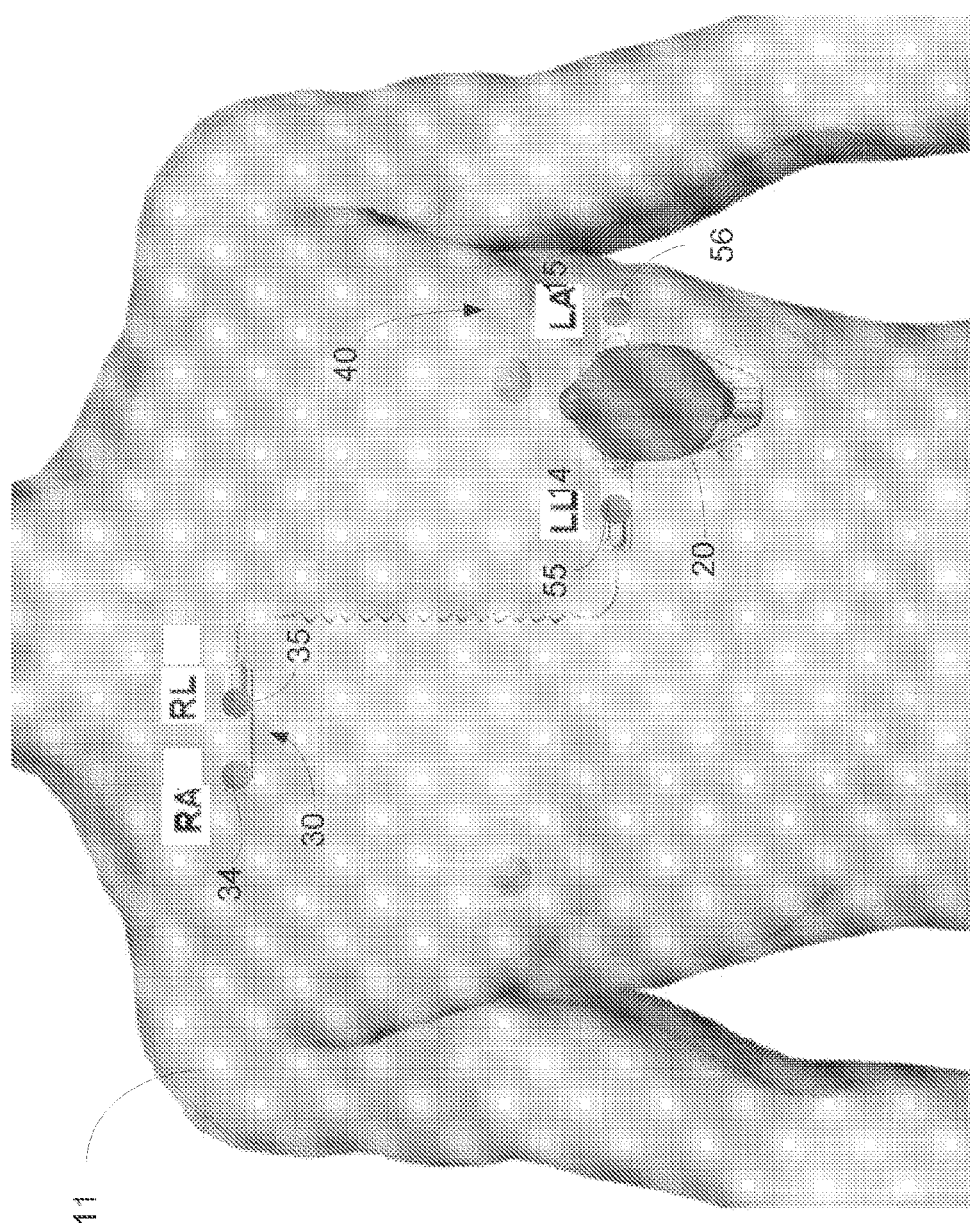
FIG. 1 illustrates a patient that wears an electrocardiograph system positioned at a lower configuration according to an embodiment of the invention.
Figure 2:
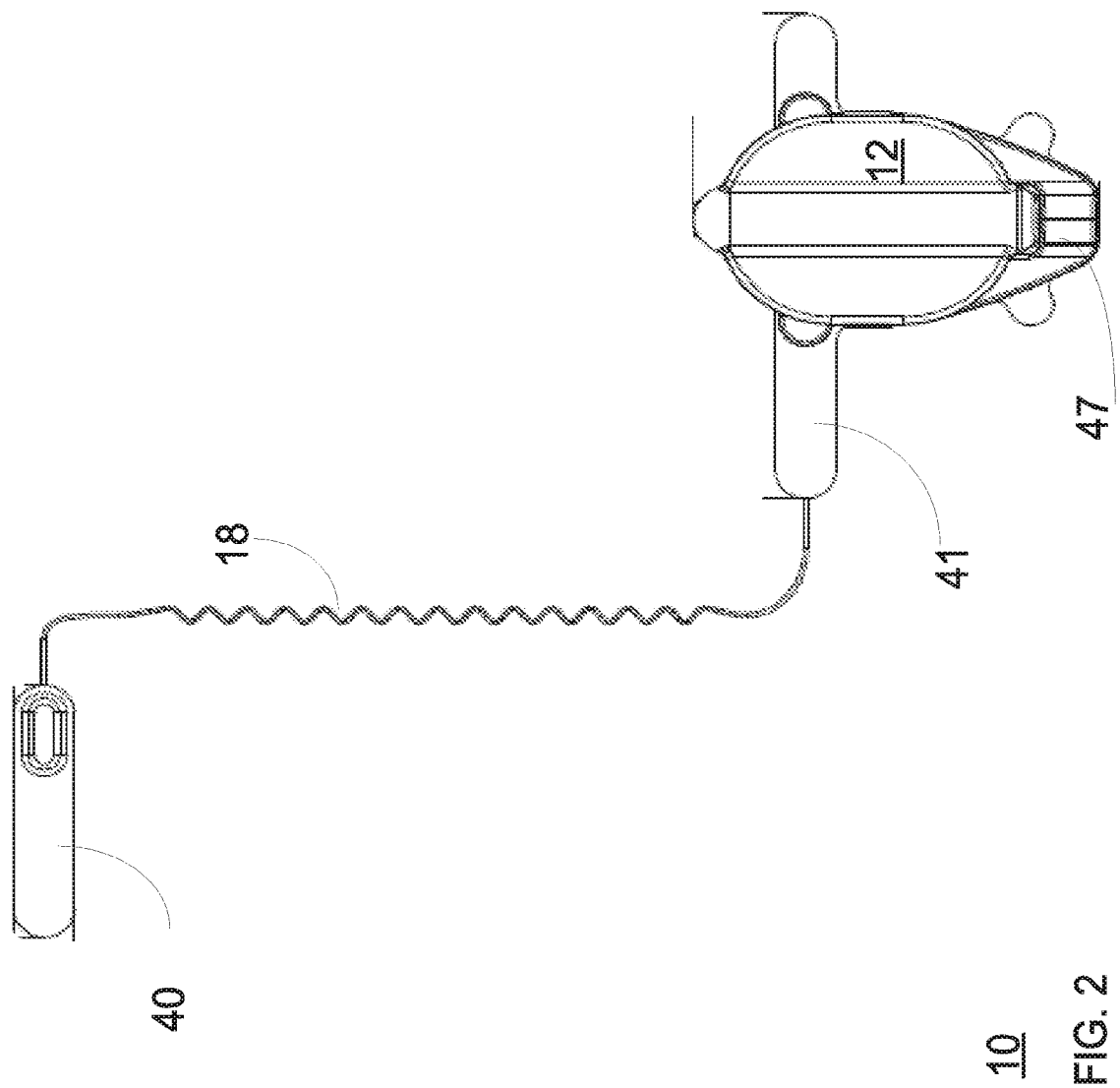
FIG. 2 is a isometric view of an electrocardiograph system positioned at a lower configuration according to an embodiment of the invention.
Figure 3:
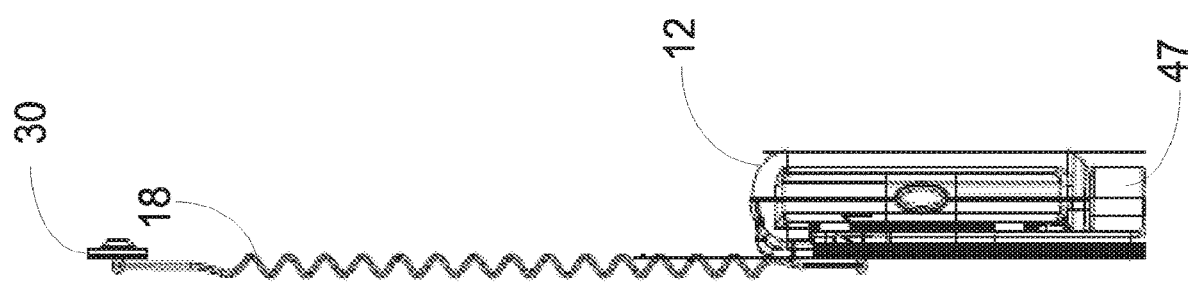
FIG. 3 is a side view of an electrocardiograph system positioned at a lower configuration according to an embodiment of the invention.
Figure 4:
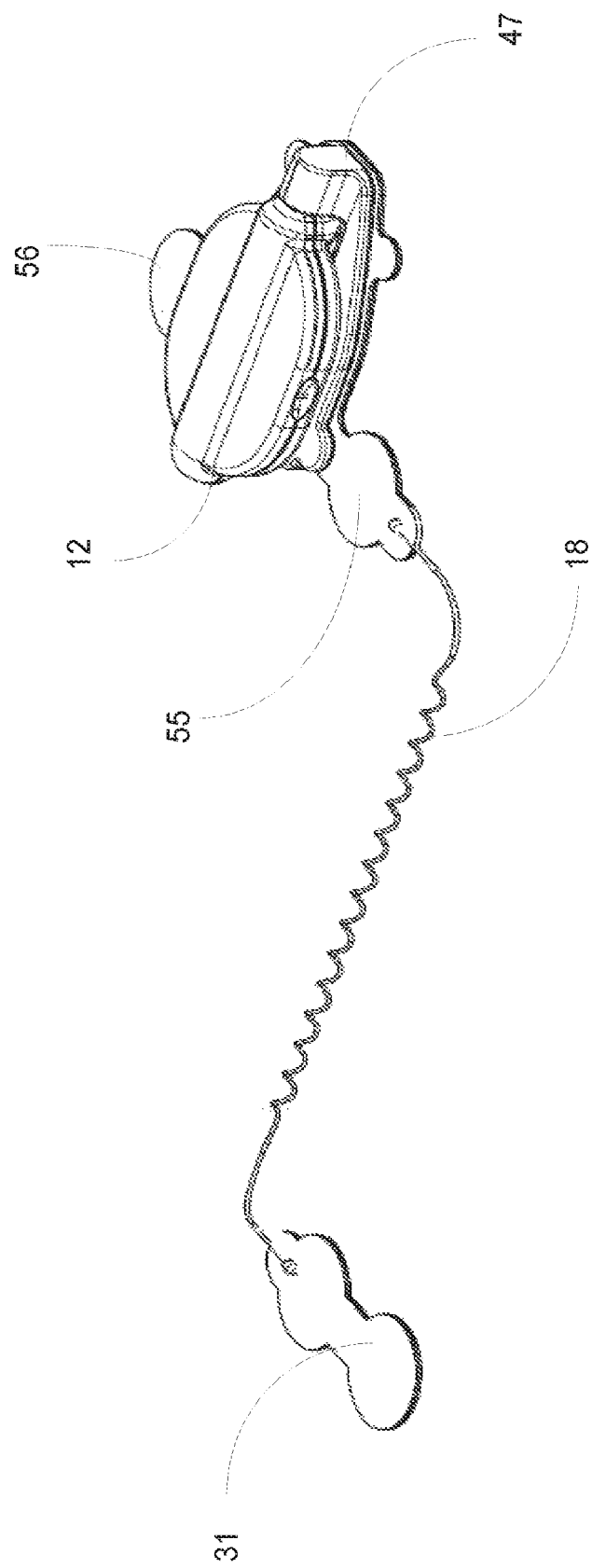
FIG. 4 is a isometric view of an electrocardiograph system positioned at a lower configuration according to an embodiment of the invention.
Figure 6:
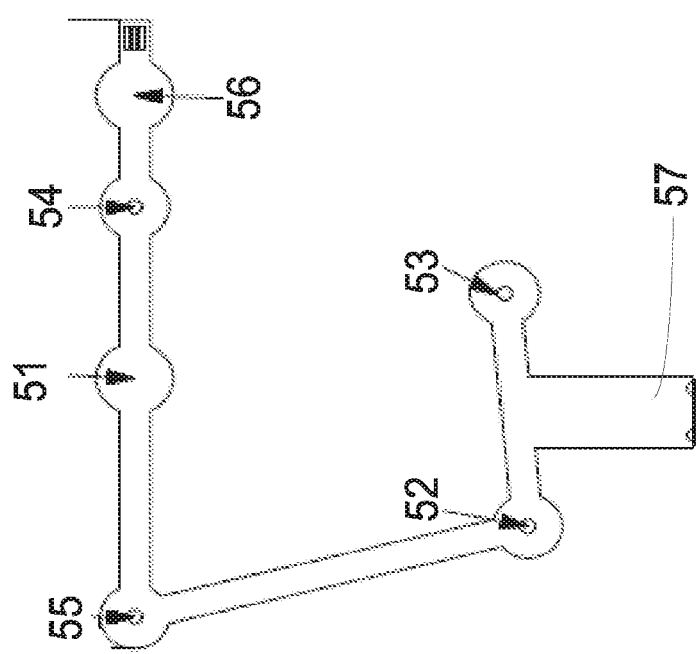
FIG. 6 illustrates a first electrical circuit according to an embodiment of the invention.
Figure 7:
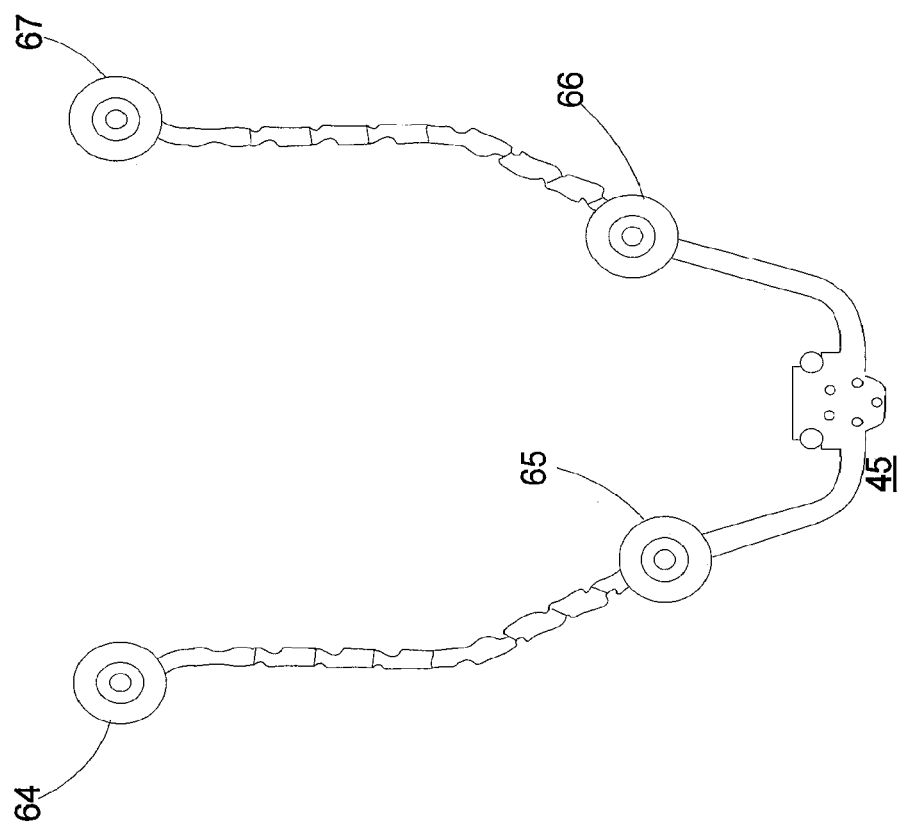
FIG. 7 illustrates a second electrical circuit according to an embodiment of the invention.
Figure 8:
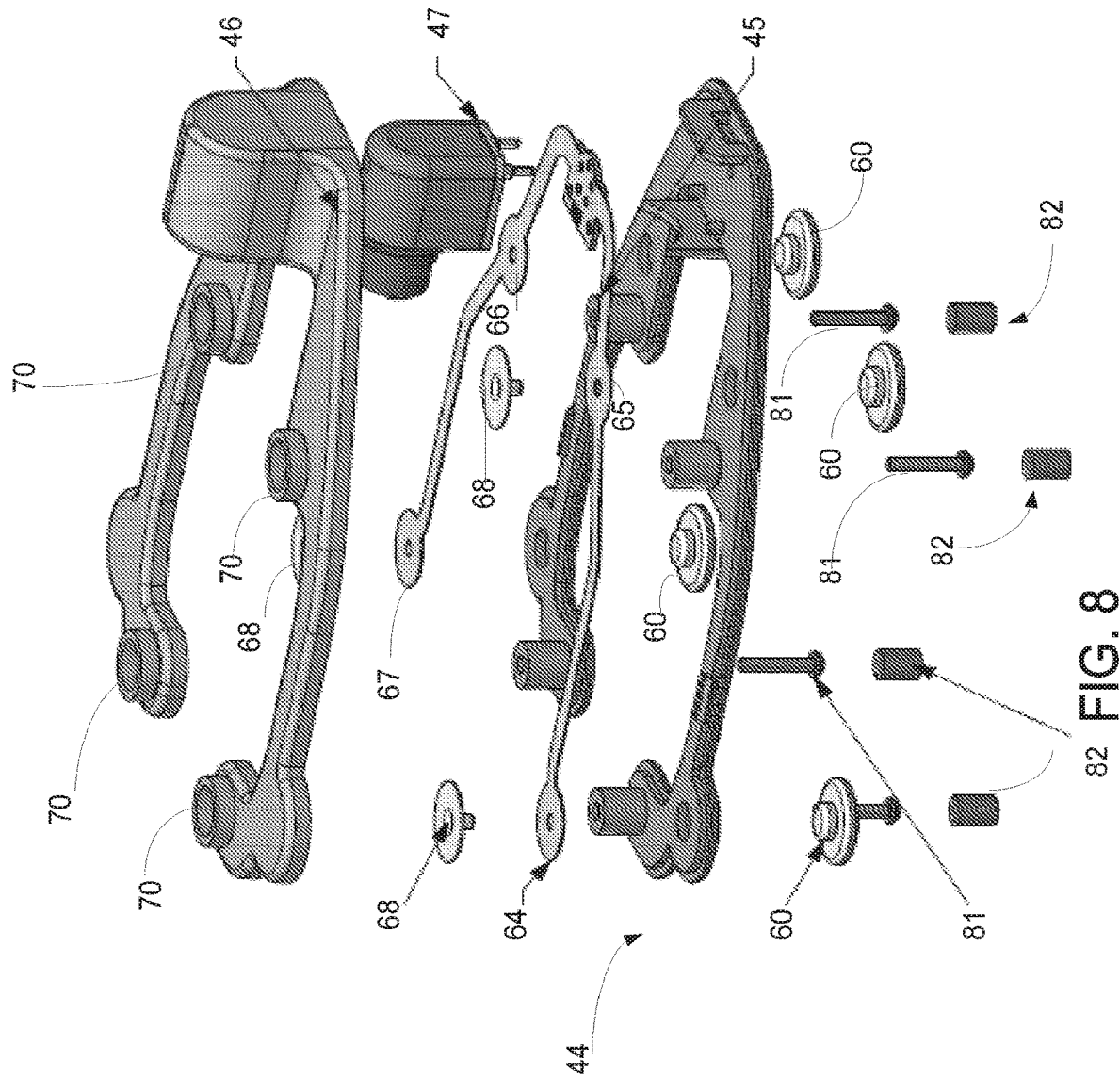
FIG. 8 is an exploded view of some layer of a second part of the electrocardiograph system according to an embodiment of the invention.
Figure 9:
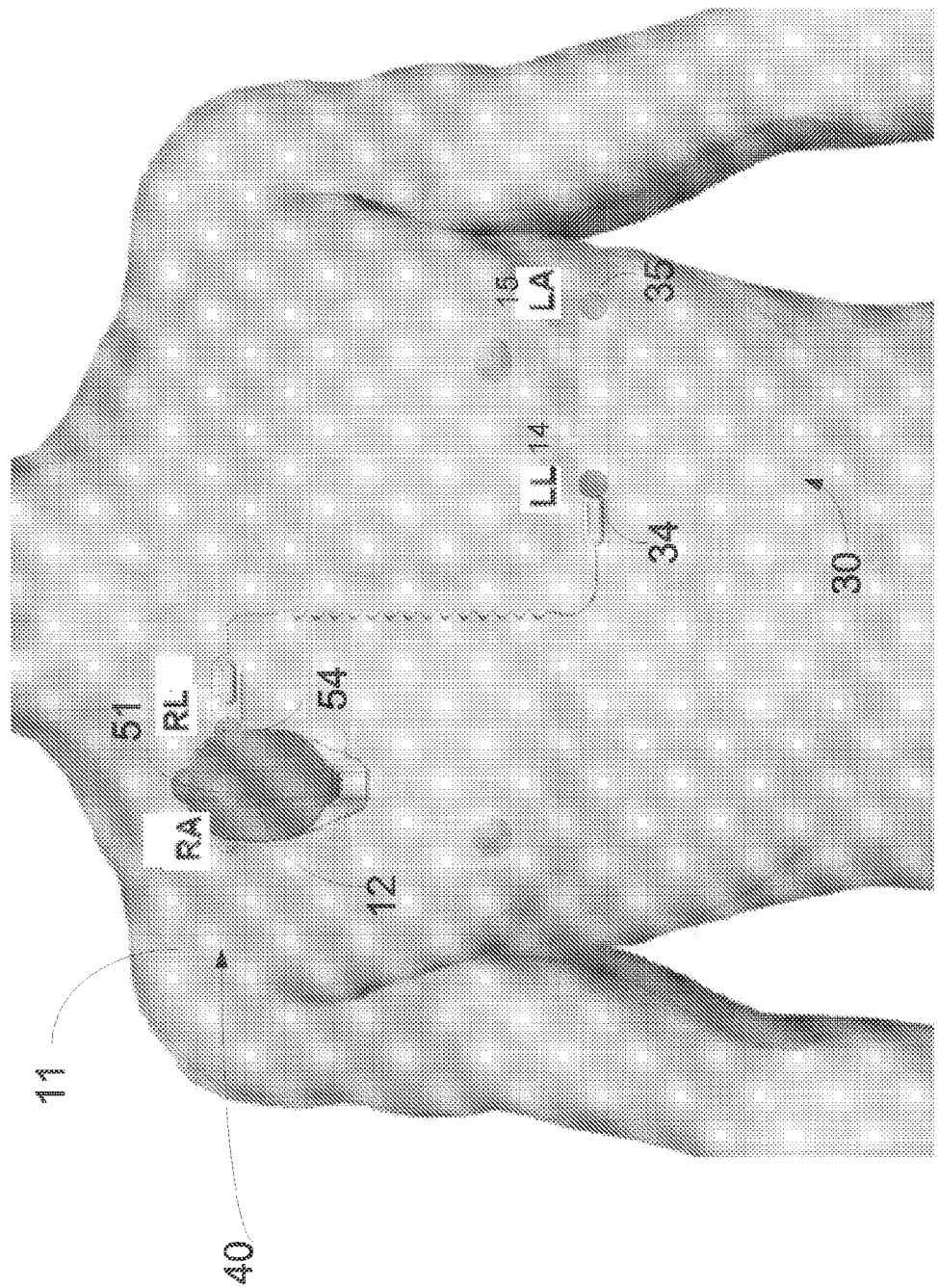
FIG. 9 illustrates a patient that wears an electrocardiograph system positioned at an upper configuration according to an embodiment of the invention.
Figure 10:
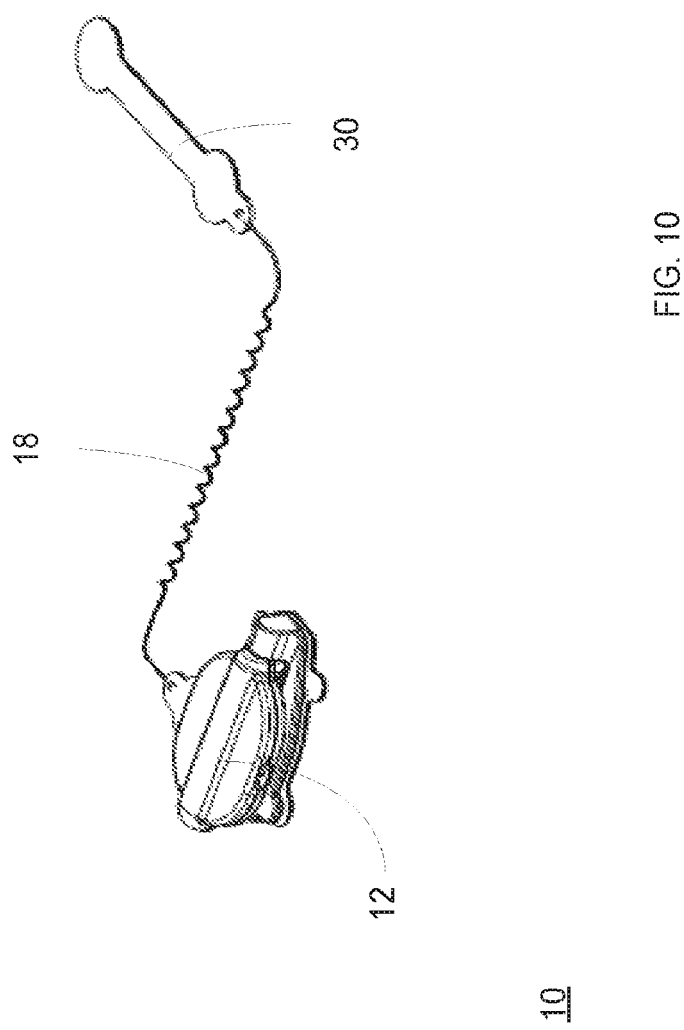
FIG. 10 is a isometric view of an electrocardiograph system positioned at an upper configuration according to an embodiment of the invention.
Figure 11:
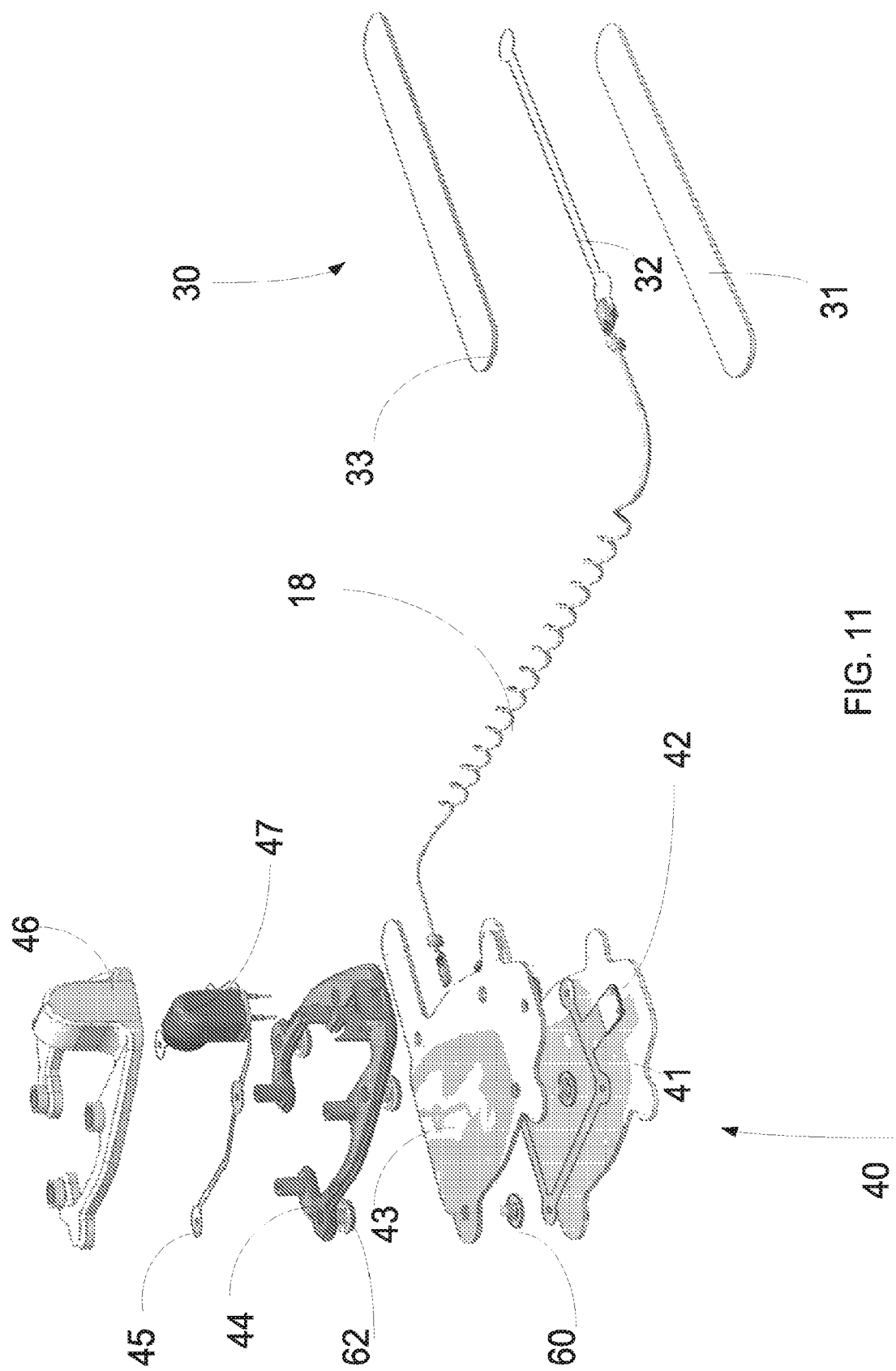
FIG. 11 is an exploded view of an electrocardiograph system without an electrocardiograph device position at an upper configuration according to an embodiment of the invention.

FIG. 1 illustrates a patient 11 that wears an electrocardiograph system 10 positioned at a lower configuration according to an embodiment of the invention. FIG. 2 is an isometric view of an electrocardiograph system 10 positioned at a lower configuration according to an embodiment of the invention. FIG. 3 is a side view of an electrocardiograph system 10 positioned at a lower configuration according to an embodiment of the invention. FIG. 4 is an isometric view of an electrocardiograph system 10 positioned at a lower configuration according to an embodiment of the invention. FIG. 5 is an exploded view of an electrocardiograph system 10 without an electrocardiograph device position at a lower configuration according to an embodiment of the invention. FIG. 6 illustrates a first electrical circuit 42 according to an embodiment of the invention. FIG. 7 illustrates a second electrical circuit 45 according to an embodiment of the invention. FIG. 8 is an exploded view of some layer of a second part of the electrocardiograph system 10 according to an embodiment of the invention. FIG. 9 illustrates a patient 11 that wears an electrocardiograph system 10 positioned at an upper configuration according to an embodiment of the invention. FIG. 10 is an isometric view of an electrocardiograph system 10 positioned at an upper configuration according to an embodiment of the invention. FIG. 11 is an exploded view of an electrocardiograph system 10 without an electrocardiograph device position at an upper configuration according to an embodiment of the invention.

When positioned at an upper position the second part 40 is positioned above the first part 30. When positioned at a lower position the second part 40 is positioned below the first part 30.

The following table provides a list of reference numbers and the elements associated with the reference numbers.

TABLE 1

| | |
|---|---|
| 10 | Electrocardiographic system |
| 11 | Patient |

TABLE 1-continued

| | |
|---|---|
| 12 | Electrocardiographic device |
| 14, 234, 433 | LL - lectrode located at electrode connection location on the intersection of the left medial clavicular line and the fifth intercostal space and is commonly referred to as V4 |
| 15, 231, 431 | LA - electrode connection location on the intersection of the fifth intercostal space and left median-axillar line and is commonly referred to as V6 |
| 235 | RA - reference electrode (FIGS. 2, 9 and 12) |
| 233, 432 | RL - electrode connection location in the second intercostal space to the right of the sternum and is commonly referred to as V1 |
| 18 | Shielded wire |
| 30 | First part of an adaptor |
| 31 | First bottom layer |
| 32 | Third electrical circuit |
| 33 | Cover layer |
| 34 | First electrode |
| 35 | Second electrode |
| 40 | Second part of an adaptor |
| 41 | Second bottom layer |
| 42 | First electrical circuit |
| 43 | Intermediate flexible layer |
| 44 | Base layer of mechanical adaptor |
| 45 | Second electrical circuit |
| 46 | Top layer of mechanical adaptor |
| 47 | Electrical connector |
| 51 | First electrical node |
| 52 | Second electrical node |
| 53 | Third electrical node |
| 54 | Fourth electrical node |
| 55 | Third electrode |
| 56 | Fourth electrode |
| 57 | Ground element |
| 60 | First set of bolts |
| 61 | Opening formed in the intermediate layer |
| 62 | Second set of bolts |
| 63 | Openings formed in the base layer of the mechanical adaptor |
| 64 | Fifth electrical node e.g., a front node |
| 65 | Sixth electrical node e.g., a rear node |
| 66 | Seventh electrical node e.g., a rear node |
| 67 | Eighth electrical node e.g., a front node |
| 68 | Top element bolts |
| 69 | Hollow support elements formed in the base layer of the mechanical adaptor |
| 70 | Screw housing (also referred to as screw cover). Formed in the top layer of the mechanical adaptor |
| 81 | Screws |
| 82 | Sealing elements positioned below the screws (also referred to as screw cover). |
| 90 | Male connector |
| 91 | Pins of male connector |
| 92 | Locking pins of male connector |
| 93 | Female connector |
| 94 | Recess - corresponds to the locking pins of the male connector |
| 95 | Tunnels (openings) of the female connector |

According to an embodiment of the invention there may be provided a detachable electrocardiographic system 10 that may include an adaptor that includes a first part 30, and a second part 40.

The first part 30 may include:

a. A first housing that may include a cover layer 33 and first bottom layer 31 that are elastic and has an underside provided with an adhesive material.

b. A first set of electrodes (such as first and second electrodes 34 and 35) that is located within the first housing. The first set of electrodes may include at least one electrode.

The second part 40 that may include:

a. A second housing that may include a second bottom layer 41 that has an underside provided with an adhesive material and a mechanical adaptor.

b. A second set of electrodes (such as electrodes 55 and 56) that are located within the second housing. The second set of electrodes may include at least one second electrode and are included in first electrical circuit 42. The first electrical circuit 42 also include first till fourth nodes 51-54 for receiving signals from first till fourth electrodes 34, 35, 55 and 56 via conductors. It (42) also includes a ground element that may be grounded (for example may be coupled to the reference electrode and/or to a ground conductor of the electrical connector 47).

c. A mechanical adaptor that is arranged to be detachably connected to an electrocardiographic device 12 that may include a processor and a wireless transmitter. The mechanical adaptor includes a base layer 44 and a top layer 46. The base layer 44 has openings 63 for allowing conductive (metallic) bolts 62 of a second set of bolts to pass therethrough.

d. An electrical connector 47 that is arranged to be detachably connected to the electrocardiographic device and to electrically couple the electrocardiographic device to conductors that convey signals from the first and second sets of electrodes.

Signals from the first part 30 should reach the second part 40. This can be done by using wireless communication (short range wireless transmitter or transceiver included in the first part 30 and short range wireless receiver or transceiver located in second part 40). Alternatively, the first and second parts 30 and 40 can be connected by wire—such as shielded and elastic wire 18. The wire 18 is shielded in the sense that the conductors that convey signals from electrodes 34 and 35 are shielded from electromagnetic interference. Once reaching the second part 40 the signals can propagate through conductors of the first and second electrical circuits 42 and 45 and through inter-layer conductors such as bolts 60 and 62 of first and second sets of bolts.

FIGS. 5, 8 and 11 illustrate the second part as also including intermediate flexible layer 43 and second electrical circuit 45. The second electrical circuit 45 includes fifth till eighth nodes 64-67 for receiving signals from first till fourth electrodes 34, 35, 55 and 56-13 these signals are conveyed via conductors and via bolts 60 and 62 of first and second sets of bolts. These signals are provided to electrical connector 47 that is detachably connected to the detachable electrocardiograph device 12.

The first and second electrodes 34 and 35 of the first part 30 are electrically coupled to the electrical connector 47 via conductors of the third electrical circuit 32, shielded wire 18, conductors that are coupled to the first electrical circuit (provide such signals to second and third nodes 52 and 53), two rear bolts 60 of the first set of bolts, two rear bolts 62 of the second set of bolts, two rear nodes 65 and 66 of the second electrical circuit and conductors of the second electrical circuit (from nodes to the electrical connector).

The third and fourth electrodes 55 and 56 of the second part 40 are electrically coupled to the electrical connector 47 conductors that are coupled to the first electrical circuit (provide such signals to first and fourth nodes 51 and 54), two front bolts 60 of the first set of bolts, two front bolts 62 of the second set of bolts, two front nodes 64 and 67 of the second electrical circuit and conductors of the second electrical circuit (from nodes to the electrical connector).

The bolt 62 of the second set of bolts and the fourth till eighth nodes 64-67 are pressed against the base layer of mechanical adaptor 44 by bolts 62 that interface with the lower surface of the top layer of the mechanical adaptor 46.

The base layer of the mechanical adaptor 44, the top layer of the mechanical adaptor 46 and the second electrical circuit may be fastened to each other by screws 81 that pass through base and top layers 44 and 46. These screws may be sealed by sealing covers 82. The screws may also lock the electrocardiograph device 12 to the adaptor.

The intermediate flexible layer 43 may cover (overlap, partially overlap) the second bottom layer 41 and provide mechanical protection to the first electrical circuit. It has openings 61 for allowing conductive (metallic) bolts 60 of a first set of bolts to pass therethrough.

In FIGS. 5, 8 and 11 the order of layers, starting from bottom to top is:
 a. Second bottom layer 41.
 b. First electrical circuit 42.
 c. Intermediate flexible layer 43.
 d. Base layer of mechanical adaptor 44.
 e. Second electrical circuit 45.
 f. Top layer of mechanical adaptor 46.

It is noted that the electrical circuits (45, 42) can be replaced by other wiring elements. In FIGS. 1 and 9 the first and second sets of electrodes essentially consist of electrodes located on a body of a patient substantially at the following electrodes connection locations: (a) in the second intercostal space to the right of the sternum, (b) on the intersection of the left medial clavicular line and the fifth intercostal space, (c) on the intersection of the fifth intercostal space and left median-axillar line.

The first and second sets of electrodes essentially consist of: (a) a first electrode that is substantially located on the intersection of the fifth intercostal space and left median-axillar line; (b) a second electrode that is substantially located on the body of the patient in the second intercostal space to the right of the sternum; and (c) a third electrode that is substantially located on the body of the patient on the intersection of the left medial clavicular line and the fifth intercostal space; wherein: (a) a first electrocardiographic signal is detected between the second electrode and the first electrode; (b) a second electrocardiographic signal is detected between the second electrode and the third electrode; and (c) a third electrocardiographic signal is detected between the third electrode and the first electrode.

The first and second sets of electrodes essentially consist of electrodes located on a body of a patient substantially at the following electrode connection locations: (a) in the second intercostal space to the right of the sternum, (b) on the intersection of the left medial clavicular line and the fifth intercostal space, (c) on the intersection of the fifth intercostal space and left median-axillar line, and (d) a reference electrode that is substantially located in proximity to an electrode of the electrode group that is located in the second intercostal space to the right of the sternum.

The second set electrodes essentially consist of electrodes located on a body of a patient substantially at the following electrode connection locations: (a) on the intersection of the left medial clavicular line and the fifth intercostal space and (b) on the intersection of the fifth intercostal space and left median-axillar line, and wherein the first set of electrodes essentially consists of an electrode and a reference electrode located on the body of the patient substantially at a second intercostal space to the right of the sternum.

The first set electrodes essentially consist of electrodes located on a body of a patient substantially at the following electrode connection locations: (a) on the intersection of the left medial clavicular line and the fifth intercostal space and (b) on the intersection of the fifth intercostal space and left median-axillar line, and wherein the second set of electrodes essentially consists of an electrode and a reference electrode located on the body of the patient substantially at a second intercostal space to the right of the sternum.

The detachable electrocardiographic system may include shielding elements for shielding the conductors that convey signals from the first and second sets of electrodes to the electrical connector.

Figure 12:
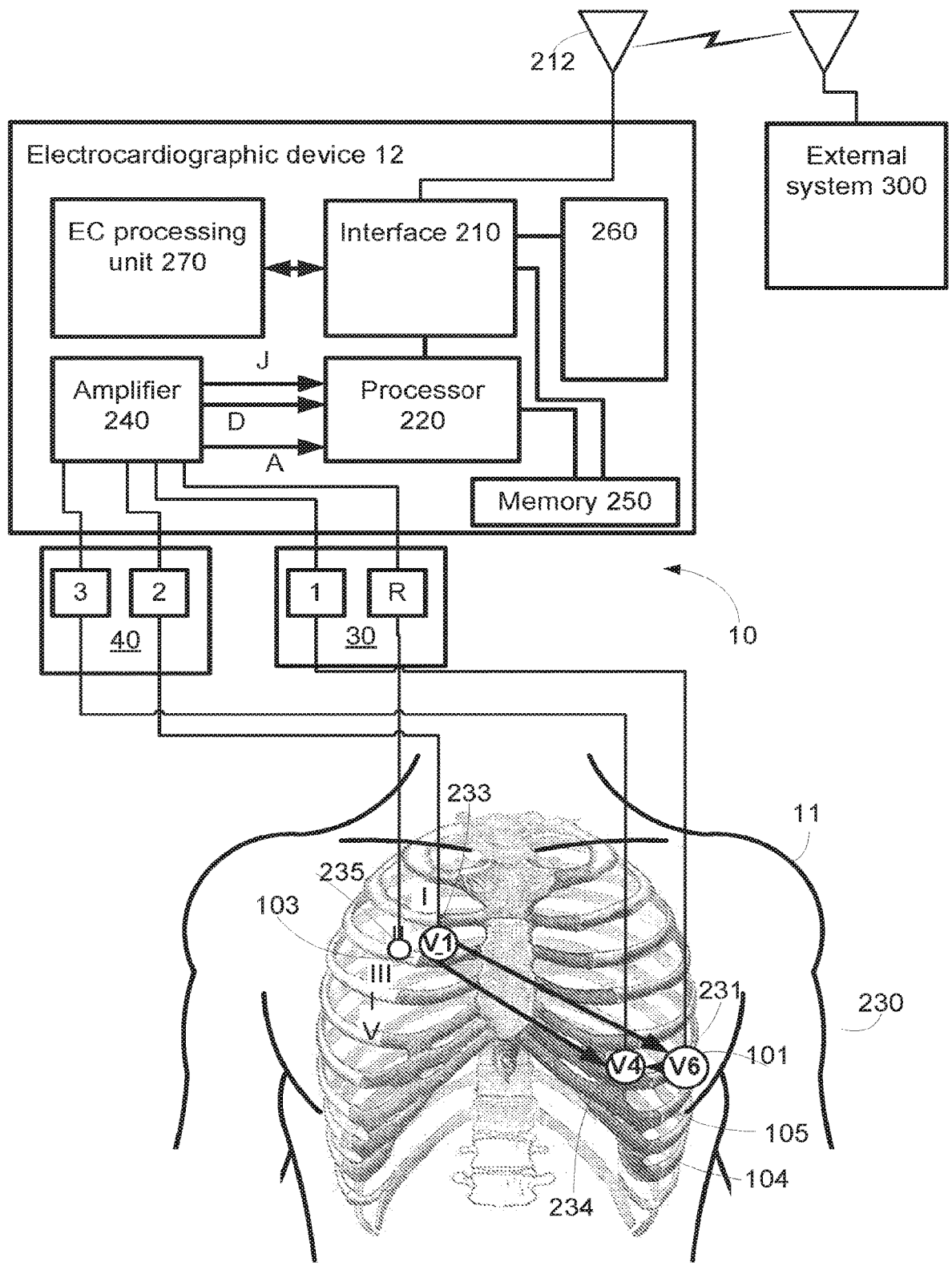
FIG. 12 illustrates an electrocardiogram, according to an embodiment of the invention.

The electrical connector may include a housing that is connected to the base layer of the mechanical adaptor and may include a socket that is arranged to move in relation to base layer of the mechanical adaptor Signal Processing FIG. 12 illustrates an electrocardiogram 10, according to an embodiment of the invention. Electrocardiogram system 10 includes an electrocardiogram device 12 that includes a processor 220 and interface 210. System 10 also includes first and second parts 30 and 40. For simplicity of explanation shielded wire 18 was not shown.

Processor 220 is adapted to receive electrocardiographic signals and to provide electrocardiographic information in response to the electrocardiographic signals, wherein each of the electrocardiographic signals is detected between a different pair of electrodes out of an electrode group 230 that substantially consists of electrodes located on a body of a patient substantially at the following electrodes connection locations: (a) in the second intercostal space to the right of the sternum (denoted 103), (b) on the intersection of the left medial clavicular line and the fifth intercostal space (denoted 104), (c) on the intersection of the fifth intercostal space and left median-axillar line (denoted 101). Electrode group 230 can also include one or more reference electrodes.

Referring to accepted electrocardiography 12-leads electrograph electrode connection locations, it is clear to a person who is skilled in the art that: (a) the electrode connection location in the second intercostal space to the right of the sternum is commonly referred to as V1; (b) the electrode connection location on the intersection of the left medial clavicular line and the fifth intercostal space is commonly referred to as V4; and (c) the electrode connection location on the intersection of the fifth intercostal space and left median-axillar line is commonly referred to as V6.

It is noted that electrode group 230 can belong to electrocardiography system 10 or be connected to such a system. The electrodes that form electrode group 230 can be detachably connected to such a system but this is not necessarily so.

Figure 15:
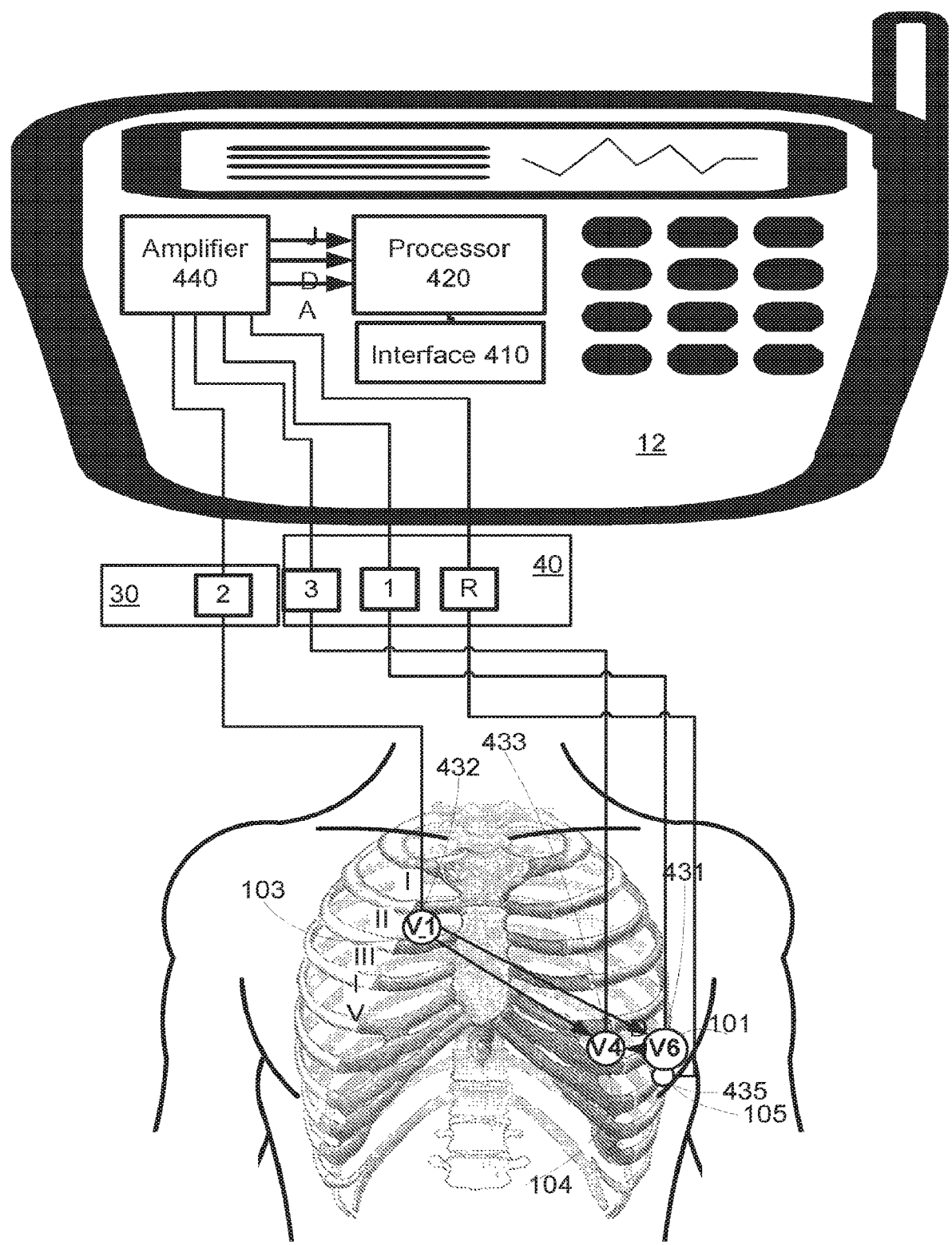
FIG. 15 illustrates an electrocardiographic system, according to an embodiment of the invention.
Figure 18:
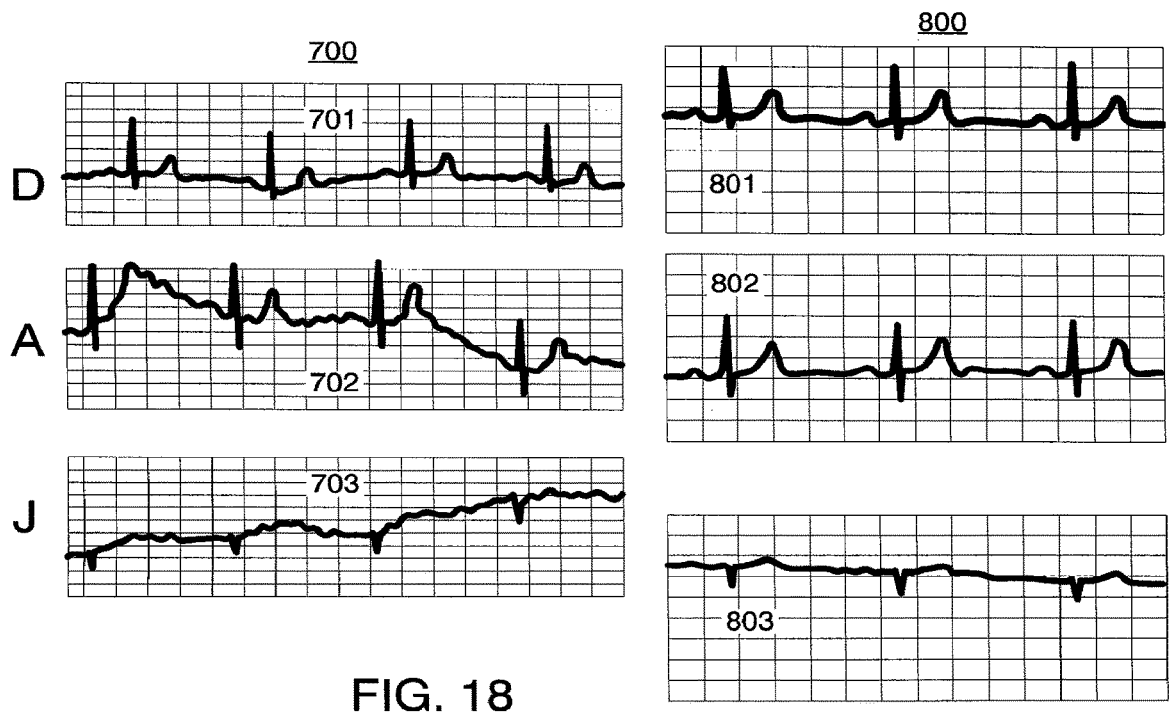
FIGS. 18-21 illustrate a comparison between cardiograms recorded by an embodiment of the electrocardiographic system, and cardiograms recorded using a standard 12 leads ECG.
Figure 19:
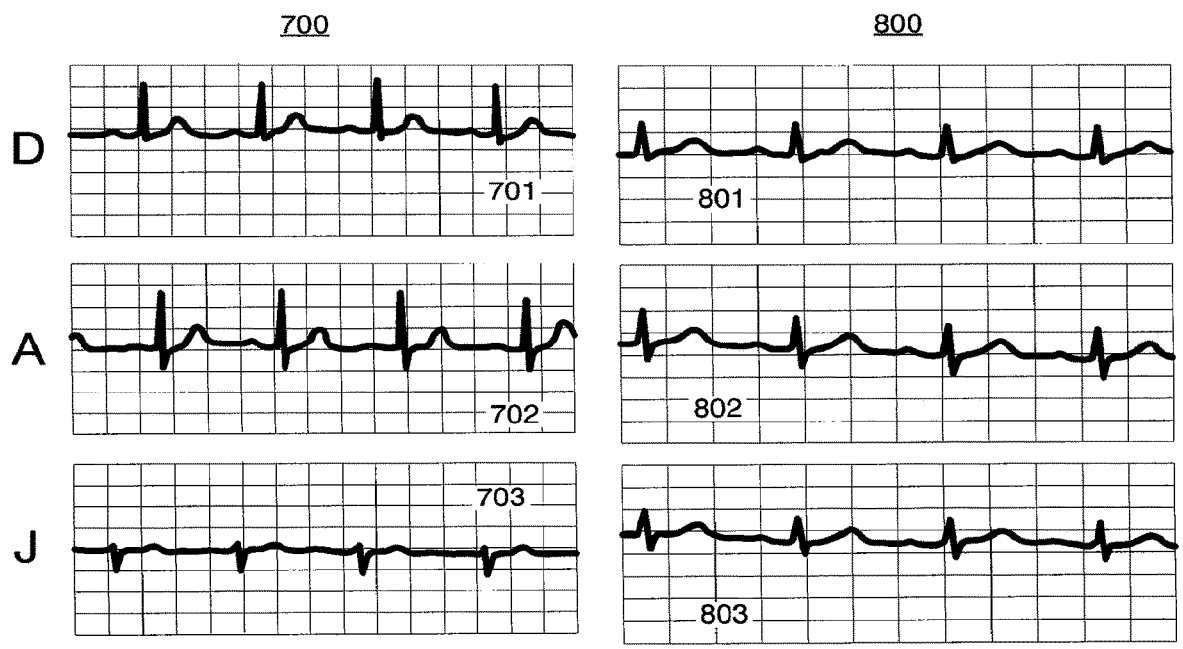
Figure 20:
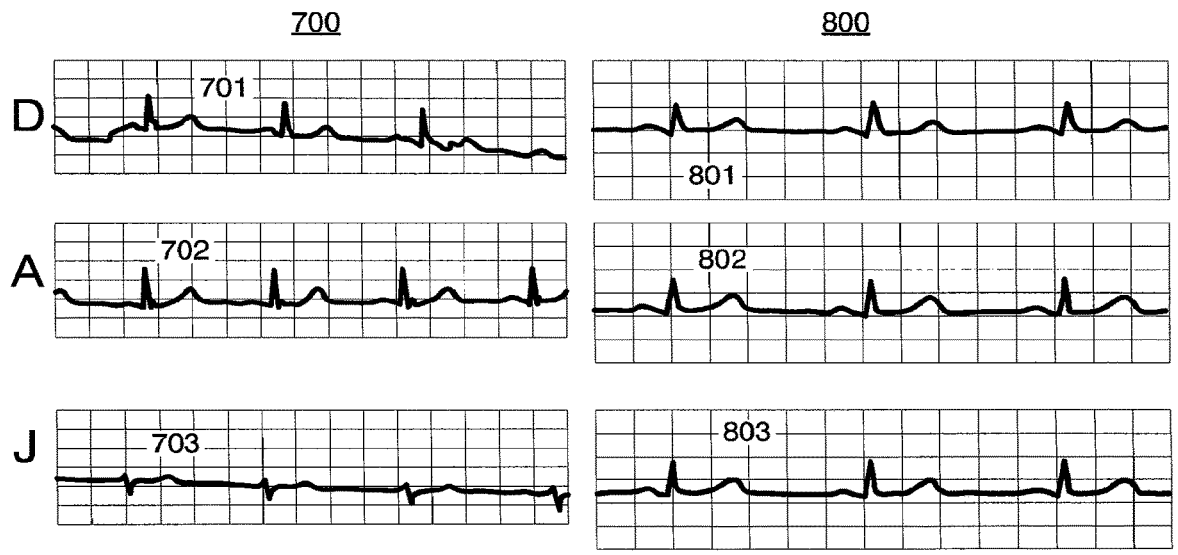
Figure 21:
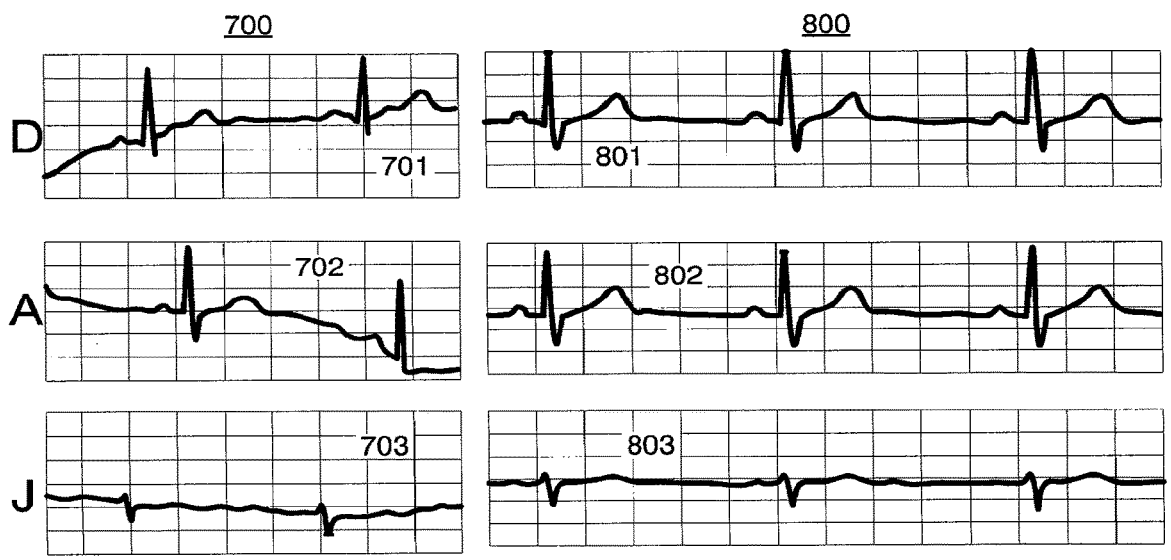

Conveniently, the electrode group 230 includes (or is connected to) three signal electrodes (first through third electrodes 231, 233, and 234) and a single reference electrode 235, wherein:
  a. First electrode 231 of electrode group 230 is substantially located on the body of the patient on the intersection of the fifth intercostal space and left median-axillar line (i.e. electrode connection location 101);
  b. Second electrode 233 of electrode group 230 is substantially located on the body of the patient in the second intercostal space to the right of the sternum (i.e. electrode connection location 103);
  c. Third electrode 234 of electrode group 230 is substantially located on the body of the patient on the intersection of the left medial clavicular line and the fifth intercostal space (i.e. electrode connection location 104); and
  d. Reference electrode 235 is substantially located on the body of the patient in proximity to any one of electrodes 232, 233 and 234 of the electrode group 230. In FIG. 12 the reference electrode is located near the second electrode 233—is substantially located on the body of the patient in the second intercostal space to the right of the sternum. In FIG. 15 the reference electrode is located near first and third electrodes.

According to such an embodiment of the invention, the electrocardiographic signals detected are conveniently: (a) a first electrocardiographic signal (also referred to a D-electrocardiographic signal) is detected between second electrode 233 and first electrode 231; (b) a second electrocardiographic signal (also referred to as A-electrocardiographic signal) is detected between second electrode 233 and third electrode 234; and (c) a third electrocardiographic signal (also referred to as J-electrocardiographic signal) is detected between third electrode 234 and first electrode 231. An electrocardiographic signal is detected as the difference between voltage levels detected by a pair of electrodes.

It is noted that, according to an embodiment of the invention, since both the first and the third electrocardiographic signals are detected between first electrode 231 and another electrode, the first and the third electrocardiographic signals are detected at different times.

Furthermore, according to an embodiment of the invention, first electrode 231 is adapted to serve as a positive electrode during a detecting of the first electrocardiographic signal, and as a negative electrode during a detecting of the third electrocardiographic signal (or vice versa).

It is noted that the first electrocardiographic signal (denoted D) conveniently characterizes a potential of a posterior wall of a left ventricle of a heart of the patient.

Similarly, the second electrocardiographic signal (denoted A) conveniently characterizes a potential of an anterior wall of the left ventricle, and the third electrocardiographic signal (denoted J) conveniently characterizes a diaphragmal surface of the heart.

Table 2 illustrates a positioning of electrodes 230, according to an embodiment of the invention.

TABLE 2

| Lead pairs (Nehb adapted) | | D | A | J |
|---|---|---|---|---|
| Red (−) | V1 | X | X | |
| Black (+) | V4 | | X | X |
| Yellow (+/−) | V6 | X | | X |
| Green (G) | Close to V6 | Ground | Ground | Ground |

As aforementioned, first electrode 231 can use for detecting of the first and the third electrocardiographic signals having opposite polarities in each case. For example, according to an embodiment of the invention wherein second electrode 233 serves as a negative terminal and fourth electrode serves as a positive terminal 234 (thus enabling detection of A-electrocardiographic signal), first electrode 231 serves as a positive terminal during a detecting of the first electrocardiographic signal, thus enabling the detection of D-electrocardiographic signal, as a negative terminal during a detecting of the third electrocardiographic signal, thus enabling the detecting of J-electrocardiographic signal.

It is noted that the same could be achieved by an additional fourth electrode (not illustrated) that is located in an immediate proximity to first electrode 231, even though it is conveniently achieved by a single first electrode 231. However, according to such an embodiment of the invention, as first electrode 231 and the fourth electrode need to be located on the body of the patient in immediate proximity to each other, it is noted that according to an embodiment of the invention, first electrode 231 and the fourth are incorporated into an electrodes assembly (not shown), which is adapted to be connected to the body of the patient, and to ensure electrical connectivity of the electrodes incorporated in which to the matching electrodes connection locations, as well as to isolate the electrodes incorporated in the electrodes assembly from each other.

According to different embodiments of the invention, the electrodes assembly includes any subgroup of a group of proximate electrodes that includes first electrode 231, the fourth electrode, and reference electrode 235 (e.g. the electrodes assembly can include first electrode 231 and reference electrode 235).

It is noted that incorporating two or three electrodes into a single electrodes assembly can serve for two purposes. Firstly, as electrocardiographic system 10 could be conveniently used in emergency situation, where time is a crucial factor, not only does it takes less time to connect the electrodes assembly to the body of the patient, it also lessen the likelihood of an electrode misallocated due to panic, poor working conditions, etc. Secondly, a preassembled electrodes assembly facilitates a closer locating of the electrodes that needs to be as proximate as possible, thus increasing the accuracy of the electrocardiographic measurement.

It is noted that, conveniently, electrocardiographic system 10 is further adapted to detect at least one of the electrocardiographic signals by implementing reference electrode 235 that is substantially located in proximity to first electrode 231 (i.e., in the proximity of electrode connection location 101). It is noted that according to other embodiments of the invention, reference electrode 235 is located elsewhere on the body of the patient, such as (though not necessarily) in proximity to second electrode 233 or in proximity to third electrode 234, wherein an appropriate electrodes assembly could incorporate the reference electrode as well as one of the third and the fourth electrodes.

Conveniently, the connection location of reference electrode 235 to the body of the patient is less significant than those of the other electrodes. The connection location of reference electrode 235 may be determined in response to a convenience of connection reference electrode 235 to the body of the patient, to facilitate quick connection of the electrodes of the electrode group 230, and hence quick detecting of the electrocardiographic signals.

It is noted that, according to an embodiment of the invention, electrocardiographic system 10 further includes amplifier 240, that is adapted to amplify at least one of the electrocardiographic signals prior to the receiving of the at least one of the electrocardiographic signals by processor 220.

Referring again to the aforementioned interface 210, interface 210 is adapted to transmit the electrocardiographic information received from processor 220. According to different embodiments of the invention, interface 210 is adapted to transmit the electrocardiographic information to a unit of electrocardiographic system 10, to external system 300 (or a unit thereof), or to both, wherein the electrocardiographic information conveniently requires further processing to provide electrocardiographically assessable information.

According to an embodiment of the invention, electrocardiographic system 10 further includes electrocardiographic processing unit 270 that is adapted to process the electrocardiographic information received from processor 220, to provide electrocardiographically assessable information.

According to an embodiment of the invention, interface 210 includes an external system interface (not shown) for the providing of the electrocardiographic information to external system 300, wherein the providing of the electrocardiographic information is provided wither via a data cable (not shown) or wirelessly (as illustrated in FIG. 12, e.g., via antenna 212). According to an embodiment of the invention, interface 210 is adapted to provide the electrocardiographic information wirelessly.

It is noted that, according to an embodiment of the invention wherein electrocardiographic system 10 includes electrocardiographic processing unit 270, interface may provide to external system 300 the electrocardiographically assessable information instead of (or on top of) the electrocardiographic information.

According to an embodiment of the invention, external system 300 is located in proximity to electrocardiographic system 10, such as when external system 300 is part of a medical emergency kit (e.g. of an ambulance etc.), or when external system 300 is adapted for the displaying of the electrocardiographic information (or the electrocardiographic assessable information), or for the printing thereof.

According to another embodiment of the invention, external system 300 is a distant external system that can reside in a hospital or in emergencies support center, and is adapted to provide the electrocardiographic information (or the electrocardiographic assessable information) to an ECG professional, for immediate assessing of the provided information. According to such an embodiment of the invention, the connection between electrocardiographic system 10 and external system 300 is conveniently a wireless one (e.g. supported by cellular telephony communication).

According to an embodiment of the invention, electrocardiographic system 10 is a compact mobile electrocardiographic system, such as a one that could be included in an emergency medical kit, or which could be stored by the patient that suffers from a severe heart condition.

Conveniently, electrocardiographic system 10 is designed for usage as a compact portable cardiographer device for express diagnostics in the situations when professional cardiological assistance is not available. Being adapted to, according to some embodiments of the invention, provide a telecommunication feature that allows a fast transferring of the recorded cardiograms to the professionals allows for faster and more adequate outpatient response in the case of emergencies.

For similar reasons, according to an embodiment of the invention, electrocardiographic system 10 further includes electrodes of electrode group 230, wherein each of the electrodes of the electrode group 230 is adapted to be detachably attached by the patient to the body of the patient at one of the electrode connection locations.

According to an embodiment of the invention, electrocardiographic system 10 further includes memory unit 250, for storing of the electrocardiographic information (or the electrocardiographic assessable information), or part of which.

It is noted that, according to an embodiment of the invention, electrocardiographic system 10 is adapted to detect the electrocardiographic signals of the patient in a normal condition and storing the relative electrocardiographic information in memory unit 250. Later, in situation of emergency, the previously stored electrocardiographic information pertaining to the normal condition could be provided by electrocardiographic system 10 along with the currently provided electrocardiographic information pertaining to the situation of emergency, thus offering an ECG professional more information upon which to analyze the provided electrocardiographic information.

According to an embodiment of the invention, electrocardiographic system 10 further includes display 260, for displaying the electrocardiographic information (or the electrocardiographic assessable information), or part of which.

It is clear to a person who is skilled in the art that the modification of the method of classic Nehb's electrode placing that is disclosed according to the herein offered invention includes placing of one or more electrodes in V6 or the immediate proximity thereof, instead of in V7. Another modification disclosed is a locating of reference electrode 235 aside a V6 electrode. Both of those modifications facilitate the implementing of electrocardiographic system 10 as a portable electrocardiographer.

It is noted that the topographic approximation of reference electrode 235 to first electrode 231 will not interfere with the quality and capability of the ECG recordings, since the direction of the leads vectors is preserved; on the other hand it will be actually of benefit when used in an electrocardiographic system 10 that is designed for emergency diagnostics of life threatening heart conditions when the rapid, reliable and simple method of ECG recording is critical.

FIGS. 13 and 14 illustrate method 500 for electrocardiographic detecting, according to an embodiment of the invention, wherein FIG. 14 illustrates different implementations of the stage of receiving, according to different embodiments of invention. It is noted that conveniently, different embodiments of method 500 are adapted to be carried out by different embodiments of electrocardiographic system 10, and as is clear to a person who is skilled in the art, method 500 could be easily adapted to support the different embodiments of electrocardiographic system 10 (some of which are discussed above), even if not specifically discussed in relation to method 500. Therefore, a person who is skilled in the art may benefit from considering method 500 and different embodiments thereof in view of the different discussed embodiments of electrocardiographic system 10.

According to an embodiment of the invention, method 500 starts with stage 510 of detecting electrocardiographic signals, wherein each of the electrocardiographic signals is detected between a different pair of electrodes out of an electrode group that substantially consists of electrodes located on a body of a patient substantially at the following electrodes connection locations: (a) in the second intercostal space to the right of the sternum, (b) on the intersection of the left medial clavicular line and the fifth intercostal space, (c) on the intersection of the fifth intercostal space and left median-axillar line.

According to an embodiment of the invention, stage 510 includes stage 511 of detecting at least one of the electrocardiographic signals by implementing a reference electrode. According to an embodiment of the invention, method 500 includes stage 520 of amplifying at least one of the electrocardiographic signals. Referring to the examples set forward in the previous drawings, stage 520 is conveniently carried out by amplifier 240.

Method 500 continues with stage 530 of receiving electrocardiographic signals, wherein each of the electrocardiographic signals is detected between a different pair of electrodes out of an electrode group that substantially consists of electrodes located on a body of a patient substantially at the following electrodes connection locations: (a) in the second intercostal space to the right of the sternum, (b) on the intersection of the left medial clavicular line and the fifth intercostal space, (c) on the intersection of the fifth intercostal space and left median-axillar line. Referring to the examples set forward in the previous drawings, stage 530 is conveniently carried out by processor 220.

According to an embodiment of the invention, stage 530 includes stage 531 of receiving the electrocardiographic signals detected between different pairs of electrodes out of the electrode group, wherein a first electrode of the electrode group is substantially located on the intersection of the fifth intercostal space and left median-axillar line, and a fourth electrode of the electrode group is located in an immediate proximity to the first electrode, wherein each of the three electrocardiographic signals is detected between a pair of electrodes selected from the electrode group which is different from a pair consisting of the first electrode and the fourth electrode. However, as disclosed above, conveniently there is no need in two electrodes, and the first electrode suffices, wherein—as aforementioned—the first electrodes may serve as a terminal having a first polarity (e.g. positive) during the detecting of the first electrocardiographic signal, and as a terminal having a second polarity (e.g. negative) during the detecting of the third signal.

According to an embodiment of the invention, stage 530 includes stage 532 of receiving the electrocardiographic signals detected between different pairs of electrodes out of the electrode group, wherein the electrode group substantially consist of: (a) a first electrode that is substantially located on the intersection of the fifth intercostal space and left median-axillar line; (b) a second electrode that is substantially located on the body of the patient in the second intercostal space to the right of the sternum; and (c) a third electrode that is substantially located on the body of the patient on the intersection of the left medial clavicular line and the fifth intercostal space; wherein: (a) a first electrocardiographic signal is detected between the second electrode and the first electrode; (b) a second electrocardiographic signal is detected between the second electrode and the third electrode; and (c) a third electrocardiographic signal is detected between the third electrode and the first electrode.

According to an embodiment of the invention, stage 530 includes stage 533 of receiving the electrocardiographic signals by a compact mobile electrocardiographic system.

According to an embodiment of the invention, stage 530 includes stage 534 of receiving the electrocardiographic signals detected between different pairs of electrodes out of the electrode group, wherein each of the electrodes of the electrode group is adapted to be detachably attached by the patient to the body of the patient at one of the electrode connection locations.

Stage 530 is followed by stage 540 of providing electrocardiographic information in response to the electrocardiographic signals. It is noted that, according to an embodiment of the invention, stage 540 includes providing the electrocardiographic information by the compact mobile electrocardiographic system. Referring to the examples set forward in the previous drawings, stage 540 is conveniently carried out by processor 220.

According to an embodiment of the invention, stage 540 is followed by stage 550 of processing the electrocardiographic information to provide electrocardiographically assessable information. Referring to the examples set forward in the previous drawings, stage 540 is carried out, according to an embodiment of the invention, by electrocardiographic processing unit 270.

Method 500 continues with stage 560 of transmitting the electrocardiographic information. It is noted that, according to some embodiments of the invention, the transmitting may include transmitting the electrocardiographically assessable information instead of (or on top of) the electrographic information. Referring to the examples set forward in the previous drawings, stage 560 is conveniently carried out by interface 210.

According to an embodiment of the invention, stage 560 includes stage 561 of transmitting the electrocardiographic information wirelessly.

According to an embodiment of the invention, stage 560 includes transmitting the electrocardiographic information by the compact mobile electrocardiographic system.

FIGS. 18 through 21 illustrate a comparison between cardiograms 800 recorded by an embodiment of electrocardiographic system 10, and cardiograms 700 recorded using a standard 12 leads ECG, wherein the electrocardiographic signals illustrated therefor are the classic Nehb's electrocardiogramals Nehb's A, Nehb's D, and Nehb's J.

It is noted that in each of FIGS. 18 through 21, the topmost cardiograms are cardiogram 801 which is a D-electrocardiographic signal, and cardiogram 701 that is a Nehb's D-electrocardiographic signal; the middle cardiograms are cardiogram 802 which is an A-electrocardiographic signal, and cardiogram 702 that is a Nehb's A-electrocardiographic signal; and the bottom cardiograms are cardiogram 803 which is a J-electrocardiographic signal, and cardiogram 703 that is a Nehb's J-electrocardiographic signal, wherein each of the FIGS. 18 through 21 illustrates cardiograms detected for a different healthy patient.

A person who is skilled in the art would learn that the results illustrated in FIGS. 18 through 21 indicate a very good correlation between the ECG cardiograms recorded by a standard cardiographer with the ECG cardiograms recorded by an embodiment of electrocardiogram, using the herein disclosed adapted Nehb's leads. It is noted that these observations agree with previous prior-art studies (e.g., Seeberger M. D., et al. (1997) "The Inverse Nehb J lead increases the sensitivity of Holter Electrocardiographic monitoring for detecting myocardial ischemia." Am. J. Cardiol 80:1-5; and Osterhues, H. H., et al. (1994) "Improved detection of transient myocardial ischemia by a new lead combination: value of bipolar lead Nehb D for Holter-monitoring." Am. Heart J. 127:559-566).

As will be clear to a person who is skilled in the art, there is a practical identity of the ECG cardiograms recorded by electrocardiogram and those recorded by the standard 12-leads ECG, and presence of sufficient number of diagnostic criteria as compared to the 12-lead ECG, which allow an unambiguously determining of most of ECG parameters and diagnostic criteria.

It is by now clear to a person who is skilled in the art that the electrographic information provided by electrocardiogram proved to be very applicable and informative for ECG diagnostics, providing good correlation with standard 12 lead ECG but requiring less time for recording, as only three active leads are in use.

Being positioned on the chest in the immediate proximity to the heart, and being aligned to the anatomic position of the heart, the herein disclosed leads are very sensitive and allow accurate diagnostics of different heart conditions. Furthermore, all the active leads according to the disclosed invention are located on an anterolateral plane of a chest wall of the patient, thus requiring little anatomical window, hence making the herein disclosed technique convenient for express diagnostics of different heart conditions, including emergency cases, such as acute ischemia or arrhythmias.

Adaptation of Nehb's leads as described herein suggests several applications for ECG diagnostics. Especially valuable is the implementation of the herein disclosed systems and methods for compact cardiographers. Adapted Nehb's leads make ECG recording simple and fast, require a small anatomic window, while still allow to obtain complete cardiographic criteria necessary for the express diagnostics in the cases when the patients are far from the inpatient hospitals and it is complicated to receive fast cardiological assistance.

By way of example, electrocardiograms that are compact cardiographers of such kind can be located in dentists' offices, surgeons, gynecologists, etc. and to be used for other situations when the professional cardiological help is for any reason delayed.

According to another embodiment of the invention, the systems and methods herein disclosed can be utilized for a relatively simple self-control for chronic patients with cardiological history. By all means, timely ECG diagnostics will undoubtedly increase the chances for successful medical help to the patient in acute situations.

FIG. 15 illustrates electrocardiogram 10, according to an embodiment of the invention. Electrocardiographic system 10 includes first part 30, second part 40 and electrocardiographic device 12. Electrocardiographic device 12 may include: (a) processor 420 that is adapted to receive three electrocardiographic signals and to provide a cardiological problem indication in response to the three electrocardiographic signals, wherein each of the three electrocardiographic signals is detected between a different pair of electrodes out of electrode group that consists of three electrodes 431, electronic messages generating system integrated agent 432 and 433 located on a body of a patient; and (b) interface 410, adapted to transmit the cardiological problem indication received from processor 420.

According to an embodiment of the invention, processor 420 is adapted to provide the cardiological problem indication in response to the three electrocardiographic signals, wherein each of the three electrocardiographic signals is detected between a different pair of electrodes out of electrode group that substantially consists of three electrodes 431, electronic messages generating system integrated agent 432 and 433 located on a body of a patient substantially at the following electrodes connection locations: (a) in the second intercostal space to the right of the sternum, (b) on the intersection of the left medial clavicular line and the fifth intercostal space, (c) on the intersection of the fifth intercostal space and left median-axillar line.

According to an embodiment of the invention, system 10 is further adapted to detect at least one of the electrocardiographic signals by implementing reference electrode 435 that is, according to an embodiment of the invention, substantially located in proximity to an electrode of electrode group that is located on the intersection of the fifth intercostal space and left median-axillar line.

According to an embodiment of the invention, processor 420 is further adapted to provide electrocardiographic information in response to the three electrocardiographic signals (similarly to system 10 disclosed above). According to an embodiment of the invention, processor 420 is adapted to process the electrocardiographic information, to provide the cardiological problem indication.

According to an embodiment of the invention, interface 410 is adapted to transmit the cardiological problem indication wirelessly.

According to an embodiment of the invention, system 10 further includes amplifier 440 that is adapted to amplify at least one of the electrocardiographic signals prior to the receiving of the at least one of the electrocardiographic signals by processor 420.

According to an embodiment of the invention, electrocardiographic system 10 is a compact mobile electrocardiographic system, which is conveniently either handily portable by a medical practitioner or a first aid provider, in order to quickly diagnose a patient, or adapted to be carried by a patient in potential hazard for longer periods of time, either for analysis or for monitoring his condition. Being able to transport the data wirelessly facilitate continuing monitoring by a medical center.

According to an embodiment of the invention, processor 420 is adapted to provide an acute arrhythmias cardiological problem indication in response to the three electrocardiographic signals.

According to an embodiment of the invention, processor 420 is adapted to provide an ischemia cardiological problem indication in response to the three electrocardiographic signals.

According to an embodiment of the invention, interface 410 is adapted to transmit the cardiological problem indication to a handheld communication device, e.g. a cellular phone, a lap-top computer, or a personal digital assistant.

According to an embodiment of the invention, electrocardiographic system 10 further includes first, second and third electrodes 431, electronic messages generating system integrated agent 432 and 433 (and potentially also reference electrode 435), wherein, according to an embodiment of the invention, the three electrodes 431, 432 and 433 (and potentially also reference electrode 435) are adapted to be self-attached to a body of a patient by the patient himself. The reference electrode 435 is illustrates as being positioned near electrodes 433 and 431 but may be located near electrode 432.

Thus, a patient who is in a potential hazard can be easily trained to connect the electrodes of system 10 to his body, either for regular monitoring, or when the patient feels (or have other reason to suspect) he may suffer from a hazardous cardiological incident. Limiting the number of electrodes to four (counting reference electrode 435 as well), comparing to five electrodes which are needed for example by Holter devices, facilitates a faster connecting of the electrodes to the body of the patient (either by the patient or by other person), and ease the training required for the correct connecting of the electrodes, thus enabling a chronic cardiological patient to be trained to place the electrodes autonomously, facilitating the use of electrocardiographic system 10 as a self-usable electrocardiographic system, adapted to be owned and operated by people suffering from a heart condition.

It would be clear to a person who is skilled in the art that other components and abilities disclosed in relation to system 10 and to different embodiments thereof could also be applied to system 10 and to different embodiments thereof, mutatis mutandis.

It is noted that conveniently, system 10 and different embodiments thereof are adapted to carry out method 900 disclosed below, and different embodiments thereof.

FIG. 16 illustrates method 900 for providing a cardiological problem indication, according to an embodiment of the invention.

According to an embodiment of the invention, method 900 starts with stage 910 of detecting at least one electrocardiographic signal of three electrocardiographic signals each of which is detected between a different pair of electrodes out of an electrode group that consists of three electrodes located on a body of a patient.

According to an embodiment of the invention, stage 910 includes stage 911 of detecting the at least one electrocardiographic signal by implementing a reference electrode that may be positioned in proximity to any electrode of the electrode group.

According to an embodiment of the invention, stage 910 is followed by stage 920 of amplifying at least one of the electrocardiographic signals.

Method 900 continues with stage 930 of receiving three electrocardiographic signals, wherein each of the three electrocardiographic signals is detected between a different pair of electrodes out of an electrode group that consists of three electrodes located on a body of a patient.

According to an embodiment of the invention, stage 930 includes stage 931 of receiving the three electrocardiographic signals, wherein each of the three electrocardiographic signals is detected between a different pair of electrodes out of an electrode group that substantially consists of three electrodes located on a body of a patient substantially at the following electrodes connection locations: (a) in the second intercostal space to the right of the sternum, (b) on the intersection of the left medial clavicular line and the fifth intercostal space, (c) on the intersection of the fifth intercostal space and left median-axillar line.

Stage 930 is conveniently followed by stage 940 of processing the three electrocardiographic signals, to determine a cardiological problem status in response to the three electrocardiographic signals.

According to an embodiment of the invention, stage 940 further includes stage 941 of processing the three electrocardiographic signals to provide electrocardiographic information (see for example discussion in relation to system 10 and to method 500).

According to an embodiment of the invention, stage 940 includes stage 942 of processing the electrocardiographic information, to provide the cardiological problem indication.

Method 900 continues with stage 950 of providing a cardiological problem indication in response to the three electrocardiographic signals. Conveniently, the cardiological problem indication is provided only if the cardiological problem status was determined problematic after processing the three electrocardiographic signals. It is noted that processing the three electrocardiographic signals suffices to detect a wide variety of cardiological problems, an early detection of which (that hopefully leads to a short door to needle span) may save the life of the patient, or significantly limit any damages of different cardiological situations.

According to an embodiment of the invention, stage 950 includes stage 951 of providing the electrocardiographic information in response to the three electrocardiographic signals (wherein the electrocardiographic information is conveniently acquired during stage 941).

According to an embodiment of the invention, stage 950 includes stage 952 of providing an acute arrhythmias cardiological problem indication in response to the three electrocardiographic signals.

According to an embodiment of the invention, stage 950 includes stage 953 of providing an ischemia cardiological problem indication in response to the three electrocardiographic signals.

Stage 950 is conveniently followed by stage 960 of transmitting the cardiological problem indication.

According to an embodiment of the invention, stage 960 further includes transmitting the electrocardiographic information (wherein it is noted that if no cardiological problem indication is generated, the electrocardiographic information could be transmitting separately).

According to an embodiment of the invention, stage 960 includes stage 961 of transmitting the cardiological problem indication wirelessly.

According to an embodiment of the invention, stage 960 includes transmitting the cardiological problem indication to a handheld communication device.

It is noted that according to an embodiment of the invention, the stages of receiving and providing (and potentially all the stages of method 900) are carried out by a compact mobile electrocardiographic system.

It would be clear to a person who is skilled in the art that other stages and details disclosed in relation to method 500 and to different embodiments thereof could also be applied to method 900 and to different embodiments thereof, mutatis mutandis.

It is noted that conveniently, method 900 and different embodiments thereof are adapted to be carry out by system 10 disclosed below, and different embodiments thereof.

FIG. 17 illustrates method 1000 according to an embodiment of the invention.

Method 1000 may start by stage 1010 of receiving by a electrocardiographic device of an electrocardiogram, signals obtained from a first part and a second part of the electrocardiogram; wherein the first part comprises: a first housing that comprises of a first bottom layer that is elastic and has an underside provided with an adhesive material; a first set of electrodes that is located within the first housing; wherein the first set of electrodes comprises at least one first electrode; wherein the second part comprises a second housing that comprises a second bottom layer that has an underside provided with an adhesive material; a second set of electrodes that are located within the second housing; wherein the second set of electrodes comprises at least one second electrode; a mechanical adaptor that is arranged to be detachably connected to the electrocardiographic device that comprises a processor and a wireless transmitter; and an electrical connector that is arranged to be detachably connected to the electrocardiographic device and to electrically couple the electrocardiographic device to conductors that convey signals from the first and second sets of electrodes.

Stage 1010 is followed by stage 1020 of providing, by the electrocardiograph device, electrocardiographic information in response to the electrocardiographic signals.

Each of the electrocardiographic signals may be detected between a different pair of electrodes out of an electrode group that substantially consists of electrodes located on a body of a patient substantially at the following electrodes connection locations: (a) in the second intercostal space to the right of the sternum, (b) on the intersection of the left medial clavicular line and the fifth intercostal space, (c) on the intersection of the fifth intercostal space and left median-axillar line; and Stage 1010 may include receiving the electrocardiographic signals detected between different pairs of electrodes out of the electrode group, wherein the electrode group substantially consist of: (a) a first electrode that is substantially located on the intersection of the fifth intercostal space and left median-axillar line; (b) a third electrode that is substantially located on the body of the patient in the second intercostal space to the right of the sternum; and (c) a fourth electrode that is substantially located on the body of the patient on the intersection of the left medial clavicular line and the fifth intercostal space; wherein: (a) a first electrocardiographic signal is detected between the third electrode and the first electrode; (b) a second electrocardiographic signal is detected between the third electrode and the fourth electrode; and (c) a third electrocardiographic signal is detected between the fourth electrode and the second electrode.

Stage 1020 may include detecting at least one of the electrocardiographic signals by implementing a reference electrode that is substantially located in proximity to an electrode of the electrode group that is located on the intersection of the fifth intercostal space and left median-axillar line.

Figure 22:
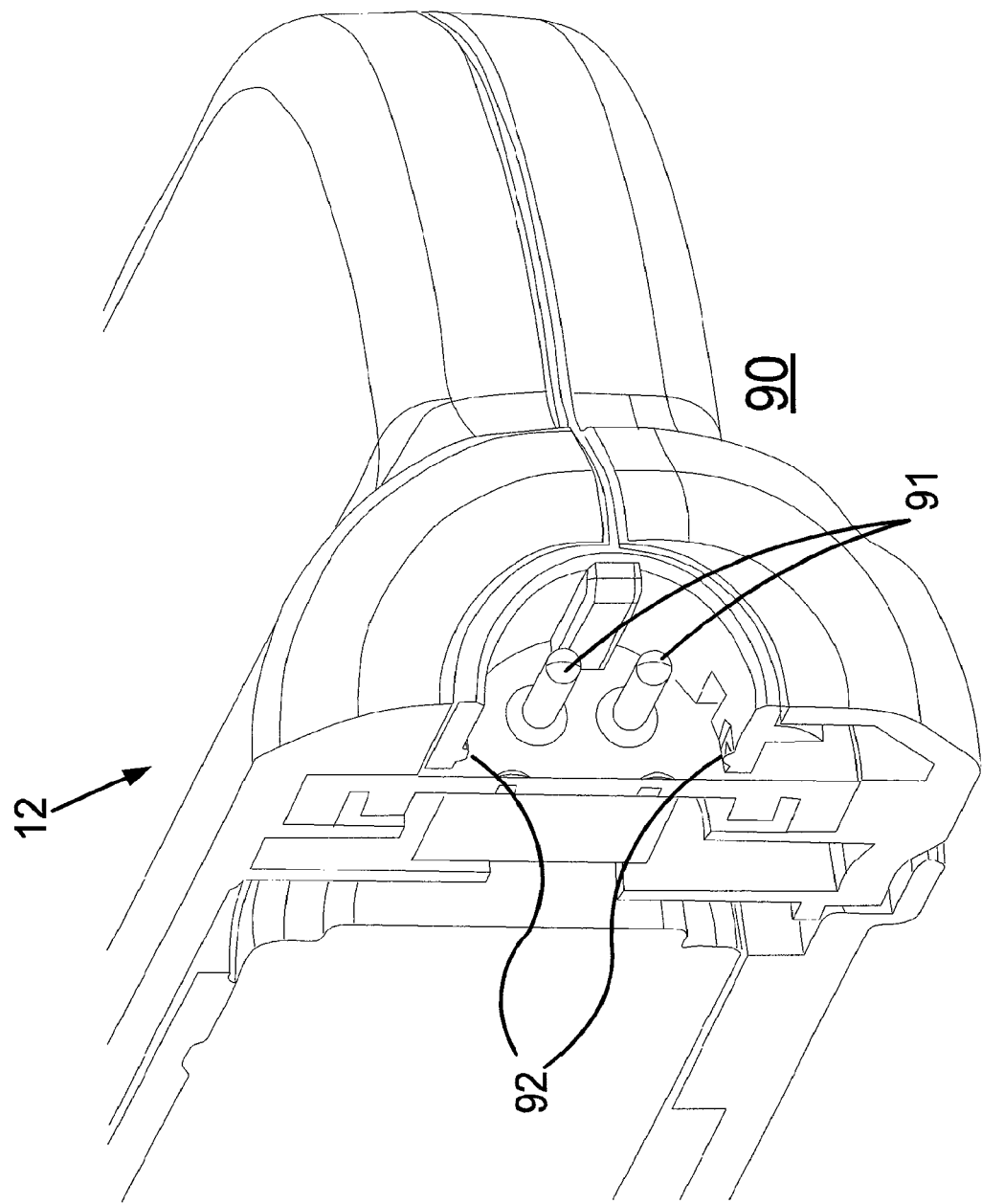
FIG. 22 is a cross sectional view of a portion of the electrocardiograph device that comprises a male connector according to an embodiment of the invention.
Figure 23:
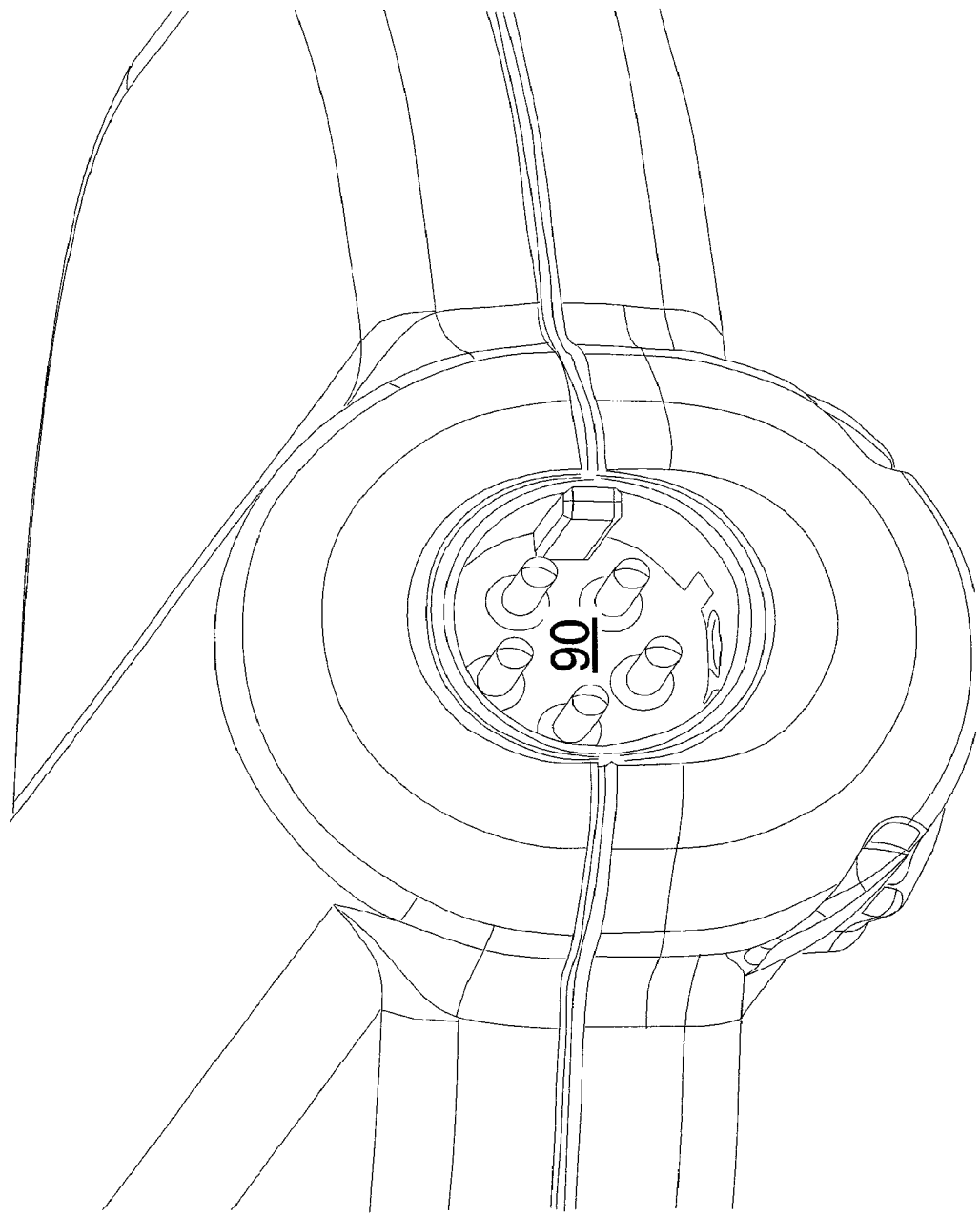
FIG. 23 is an isometric view of a portion of the electrocardiograph device that comprises a male connector according to an embodiment of the invention.

FIG. 22 is a cross sectional view of a portion of the electrocardiograph device 12 that includes a male connector 90 according to an embodiment of the invention. FIG. 23 is an isometric view of a portion of the electrocardiograph device 12 that includes a male connector 90 according to an embodiment of the invention.

Figure 24:
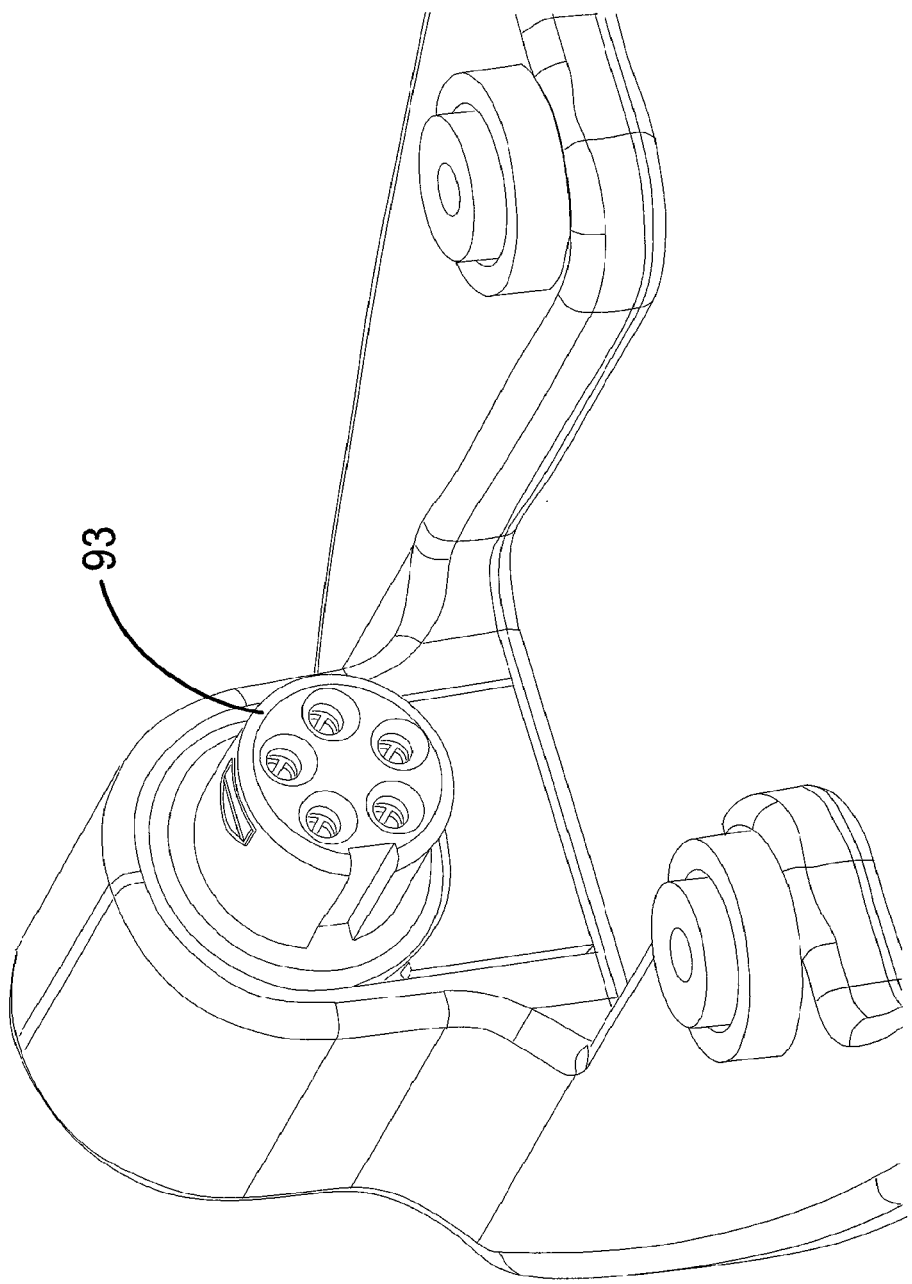
FIG. 24 is an isometric view of a portion of the mechanical adaptor that comprises a female connector according to an embodiment of the invention.

FIG. 24 is an isometric view of a portion of the mechanical adaptor that includes a female connector 93 according to an embodiment of the invention. FIG. 25 is a cross sectional view of a portion of the mechanical adaptor that includes a female connector 93 according to an embodiment of the invention.

The male connector 90 include multiple (for example five) pins 91 that fit the corresponding tunnels (openings) 95 of female connector 93. The pins are arranged to slide into the corresponding openings until the locking pins 92 of the male connector 90 enter the recess 94 that is formed at the exterior of the female connector 93 and mechanically locks the device 12 to the adaptor.

The present invention can be practiced by employing conventional tools, methodology, and components. Accordingly, the details of such tools, components, and methodology are not set forth herein in detail. In the previous descriptions, numerous specific details are set forth, in order to provide a thorough understanding of the present invention. However, it should be recognized that the present invention might be practiced without resorting to the details specifically set forth.

Only exemplary embodiments of the present invention and but a few examples of its versatility are shown and described in the present disclosure. It is to be understood that the present invention is capable of use in various other combinations and environments and is capable of changes or modifications within the scope of the inventive concept as expressed herein.

We claim:

1. A wearable electrocardiographic monitoring system for diagnosis of cardiac arrhythmia, the wearable electrocardiographic monitoring system comprising:
a first wearable unit comprising:
a processor;
a wireless transmitter connected to the processor;
an amplifier connected to the processor;
a first electrical circuit board including an electrical socket configured to electrically connect the amplifier with a first electrode, wherein the amplifier is thereby adapted to amplify electrocardiographic signals prior to the receiving of the electrocardiographic signals by the processor;
a base layer; and
a first housing comprising a first bottom layer and an intermediate flexible layer that is coupled to the the base layer by connectors, wherein the first electrical circuit board is positioned between the intermediate flexible layer and the first bottom layer and the first housing encloses the first electrical circuit board, wherein the first housing includes a first opening that exposes the electrical socket, and wherein the first housing is substantially planar and is configured to be arranged in a chest plane;

wherein the base layer is arranged adjacent to the intermediate flexible layer such that the intermediate flexible layer is positioned between the first electrical circuit board and the base layer;

wherein the connectors include inter-layer conductors that pass through the intermediate flexible layer and the base layer of the first wearable unit, and wherein the inter-layer conductors comprise metallic bolts;

a second wearable unit connected to the first wearable unit via an elongate conductor, the second wearable unit comprising:

a second electrical circuit board configured to electrically connect a second end portion of the elongate conductor to a second electrode; and a second housing enclosing the second electrical circuit board and the second end portion of the elongate conductor, wherein the second housing is substantially planar and configured to be arranged in the chest plane and offset from the first housing; and the elongate conductor extending laterally between the first housing and the second housing configured to be substantially within the chest plane, wherein the elongate conductor has a first end portion, the second end portion opposite the first end portion, and a middle portion connecting the first end portion to the second end portion, the first end portion being connected to the first electrode and enclosed within the first housing and the second end portion being connected to the second electrode and enclosed within the second housing;

wherein the middle portion of the elongate conductor is flexible and is not enclosed in the first housing or the second housing, and wherein the elongate conductor comprises a shielded wire shielded from electromagnetic interference for electrically coupling the first electrode to the second electrode.

2. The wearable electrocardiographic monitoring system of claim 1, wherein the first electrical circuit board further comprises a ground conductor that is electrically coupled to a ground input of the elongate conductor.

3. The wearable electrocardiographic monitoring system of claim 1, wherein the shielded wire electrically couples the first electrode to the second electrode of the wearable electrocardiographic monitoring system.

4. The wearable electrocardiographic monitoring system of claim 1, wherein the processor processes electrical signals from the first and second electrodes and the wireless transmitter transmits an outcome of the processing of the electrical signals.

5. The wearable electrocardiographic monitoring system of claim 1, wherein the elongate conductor is electrically connected to the first wearable unit via the electrical socket.

6. The wearable electrocardiographic monitoring system of claim 1, further comprising shielding elements for shielding the elongate conductor that conveys signals from the first and second electrodes.

7. The wearable electrocardiographic monitoring system of claim 1, wherein each of the first and second electrodes are configured to be detachably connected to a body of a patient.

8. The wearable electrocardiographic monitoring system of claim 1, further comprising a third electrode.

9. The wearable electrocardiographic monitoring system of claim 8, wherein the third electrode is configured to be detachably connected to a body of a patient.

10. The wearable electrocardiographic monitoring system of claim 1, wherein the second housing comprises a second bottom layer and a second top layer that is fastened to the second bottom layer, and wherein the second electrical circuit board is enclosed between the second top layer and the second bottom layer.

11. The wearable electrocardiographic monitoring system of claim 1, further comprising an antenna for wireless communications.

12. The wearable electrocardiographic monitoring system of claim 1, further comprising an external system interface, whereto electrocardiographic information is provided from the wireless transmitter.

* * * * *